(12) United States Patent
Rahman et al.

(10) Patent No.: US 9,909,986 B2
(45) Date of Patent: Mar. 6, 2018

(54) THICKNESS DETERMINATION AND LAYER CHARACTERIZATION USING TERAHERTZ SCANNING REFLECTOMETRY

(71) Applicant: Applied Research and Photonics, Inc., Harrisburg, PA (US)

(72) Inventors: Anis Rahman, Hummelstown, PA (US); Aunik K. Rahman, Hummelstown, PA (US)

(73) Assignee: Applied Research and Photonics, Inc., Harrisburg, PA (US)

( * ) Notice: Subject to any disclaimer, the term of this patent is extended or adjusted under 35 U.S.C. 154(b) by 0 days.

(21) Appl. No.: 14/795,663

(22) Filed: Jul. 9, 2015

(65) Prior Publication Data

US 2015/0316475 A1    Nov. 5, 2015

Related U.S. Application Data

(60) Continuation-in-part of application No. 13/281,230, filed on Oct. 25, 2011, now Pat. No. 9,093,810, which
(Continued)

(51) Int. Cl.
| | | |
|---|---|---|
| *G02F 1/35* | (2006.01) | |
| *G01N 21/55* | (2014.01) | |
| *G01N 21/95* | (2006.01) | |
| *G01N 33/483* | (2006.01) | |
| *G01N 21/3581* | (2014.01) | |

(Continued)

(52) U.S. Cl.
CPC ........... *G01N 21/55* (2013.01); *A61B 5/0507* (2013.01); *A61B 5/444* (2013.01); *B82Y 20/00* (2013.01); *G01N 21/3563* (2013.01); *G01N 21/3581* (2013.01); *G01N 21/3586* (2013.01); *G01N 21/9501* (2013.01); *G01N 33/4833* (2013.01); *G02F 1/353* (2013.01); *G02F 1/3558* (2013.01); *G01N 2021/3568* (2013.01);
(Continued)

(58) Field of Classification Search
None
See application file for complete search history.

(56) References Cited

U.S. PATENT DOCUMENTS

| | | |
|---|---|---|
| 6,078,047 A | 6/2000 | Mittleman et al. |
| 6,605,808 B2 | 8/2003 | Mickan et al. |

(Continued)

FOREIGN PATENT DOCUMENTS

JP          09274117 A     10/1997

OTHER PUBLICATIONS

Tomalia, Donald A., "Birth of a New Macromolecular Architecture: Dendrimers as Quantized Building Blocks for Nanoscale Synthetic Organic Chemistry," Aldrichmica Acta, vol. 37, No. 2, (2004), pp. 39-57.

(Continued)

*Primary Examiner* — Chad H Smith
(74) *Attorney, Agent, or Firm* — Volpe and Koenig, P.C.

(57) ABSTRACT

A terahertz scanning reflectometer system is described herein for in-situ measurement of polymer coating thickness, semiconductor wafer's surface sub-surface inspection in a non-destructive and non-invasive fashion with very high resolution (e.g., 25 nm or lower) and spectral profiling and imaging of surface and sub-surface of biological tissues (e.g., skin) in a non-invasive fashion.

8 Claims, 39 Drawing Sheets

Related U.S. Application Data is a division of application No. 11/862,474, filed on Sep. 27, 2007, now Pat. No. 8,050,531, application No. 14/795,663, filed on Jul. 9, 2015, which is a continuation-in-part of application No. 14/144,155, filed on Dec. 30, 2013, now Pat. No. 9,239,290, which is a continuation of application No. 13/423,032, filed on Mar. 16, 2012, now Pat. No. 8,620,132, and a continuation-in-part of application No. 13/281,230, filed on Oct. 25, 2011, now Pat. No. 9,093,810, which is a division of application No. 11/862,474, filed on Sep. 27, 2007, now Pat. No. 8,050,531, said application No. 13/423,032 is a continuation-in-part of application No. 12/322,662, filed on Feb. 5, 2009, now Pat. No. 8,759,778, and a continuation-in-part of application No. 11/862,473, filed on Sep. 27, 2007, now Pat. No. 7,919,755, and a continuation-in-part of application No. 11/862,474, filed on Sep. 27, 2007, now Pat. No. 8,050,531.

(60) Provisional application No. 62/022,334, filed on Jul. 9, 2014, provisional application No. 62/022,906, filed on Jul. 10, 2014, provisional application No. 60/827,206, filed on Sep. 27, 2006, provisional application No. 61/454,157, filed on Mar. 18, 2011, provisional application No. 60/827,206, filed on Sep. 27, 2006, provisional application No. 61/026,233, filed on Feb. 5, 2008.

(51) Int. Cl.
| | | |
|---|---|---|
| *B82Y 20/00* | (2011.01) | |
| *G02F 1/355* | (2006.01) | |
| *G01N 21/3586* | (2014.01) | |
| *A61B 5/05* | (2006.01) | |
| *A61B 5/00* | (2006.01) | |
| *G01N 21/3563* | (2014.01) | |
| *G02F 1/361* | (2006.01) | |
| *G02F 1/365* | (2006.01) | |

(52) U.S. Cl.
CPC ........ *G01N 2201/101* (2013.01); *G02F 1/361* (2013.01); *G02F 1/365* (2013.01); *G02F 2203/13* (2013.01)

(56) References Cited

U.S. PATENT DOCUMENTS

| | | | |
|---|---|---|---|
| 6,865,014 | B2 | 3/2005 | Ciesla et al. |
| 6,957,099 | B1 | 10/2005 | Arnone et al. |
| 7,119,339 | B2 | 10/2006 | Ferguson et al. |
| 7,145,148 | B2 | 12/2006 | Alfano et al. |
| 7,214,940 | B2 | 5/2007 | Cluff et al. |
| 7,335,883 | B2 | 2/2008 | Wallace et al. |
| 7,368,280 | B2 | 5/2008 | Zhang et al. |
| 7,381,955 | B2 | 6/2008 | Watanabe et al. |
| 7,389,029 | B2 | 6/2008 | Rahman et al. |
| 7,391,032 | B1 | 6/2008 | Hyde et al. |
| 7,480,434 | B2 | 1/2009 | Hochberg et al. |
| 7,612,341 | B2 | 11/2009 | Fitzgerald et al. |
| 7,675,036 | B2 | 3/2010 | Taday et al. |
| 7,683,778 | B2 | 3/2010 | Ouchi |
| 7,688,078 | B2 | 3/2010 | Miyazaki et al. |
| 7,710,561 | B2 | 5/2010 | Roth |
| 7,728,296 | B2 | 6/2010 | Cole et al. |
| 7,919,755 | B2 | 4/2011 | Rahman et al. |
| 8,050,531 | B2 | 11/2011 | Rahman et al. |
| 8,620,132 | B2 | 12/2013 | Rahman et al. |
| 8,759,778 | B2 | 6/2014 | Rahman |
| 2002/0074500 | A1 | 6/2002 | Mickan et al. |
| 2003/0163042 | A1 | 8/2003 | Salmon |
| 2004/0022475 | A1 | 2/2004 | Pennington |
| 2004/0065832 | A1 | 4/2004 | Cluff et al. |
| 2004/0155193 | A1 | 8/2004 | Tran et al. |
| 2005/0002628 | A1 | 1/2005 | Rahman et al. |
| 2005/0023470 | A1 | 2/2005 | Ferguson et al. |
| 2005/0082479 | A1 | 4/2005 | Wallace et al. |
| 2005/0098728 | A1* | 5/2005 | Alfano ............... G01N 21/3581 250/341.8 |
| 2006/0043298 | A1 | 3/2006 | Kawase et al. |
| 2006/0104480 | A1 | 5/2006 | Fleisher |
| 2006/0231762 | A1* | 10/2006 | Ohtake ............... G01N 21/552 250/341.8 |
| 2006/0255277 | A1 | 11/2006 | Cole et al. |
| 2006/0268945 | A1 | 11/2006 | Minamide et al. |
| 2007/0195921 | A1 | 8/2007 | Ouchi |
| 2007/0235658 | A1 | 10/2007 | Zimdars et al. |
| 2007/0257216 | A1 | 11/2007 | Withers et al. |
| 2007/0263682 | A1 | 11/2007 | Zhang et al. |
| 2007/0296957 | A1 | 12/2007 | Fitzgerald et al. |
| 2008/0006767 | A1 | 1/2008 | Taday et al. |
| 2008/0007817 | A1 | 1/2008 | Hochberg et al. |
| 2008/0017813 | A1 | 1/2008 | Vetrovec et al. |
| 2008/0099698 | A1 | 5/2008 | Rahman et al. |
| 2008/0128618 | A1 | 6/2008 | Rahman et al. |
| 2009/0022445 | A1 | 1/2009 | Hochberg et al. |
| 2009/0206263 | A1 | 8/2009 | Rahman |
| 2009/0290149 | A1 | 11/2009 | Roth |
| 2009/0314944 | A1 | 12/2009 | Evans et al. |
| 2012/0099827 | A1 | 4/2012 | Rahman |
| 2012/0228507 | A1 | 9/2012 | Rahman et al. |
| 2014/0103215 | A1 | 4/2014 | Rahman et al. |

OTHER PUBLICATIONS

Ahn, J., et al., "Terahertz waveform synthesis via optical rectification of shaped ultrafast laser pulses," Optics Express, vol. 11, No. 20, (Oct. 6, 2003), pp. 2486-2496.

Rahman, Anis, "Nanophotonic Integrated Circuit: A Platform for "Optical Processor"," web page, Applied Research and Photonics, Inc., pp. 1-18.

Website: http://prola.aps.org/abstract/PRL/v28/i14/p897_1, "Optical Rectification by Impurities in Polar Crystals," Physical Review Online Archive, Issue 14, (Apr. 1972), pp. 1-2.

Blum, Robert et al., "High-electric-field poling of nonlinear optical polymers," J. Optical Society of America B, vol. 15, No. 1, (Jan. 1998), pp. 318-328.

Boyd, Robert W., "The Nonlinear Optical Susceptibility," Nonlinear Optics Second Edition, Copyright 2003.

Cao, Hua, et al.,"Broadband generation of terahertz radiation in a waveguide," Optics Letters, vol. 29, No. 15, (Aug. 1, 2004), pp. 1751-1753.

Carr, G.L., et al., "High-power terahertz radiation form relativistic electrons," Nature, vol. 420, (Nov. 14, 2002), pp. 153-156.

Chang, Guoqing, et al., "Power Scalable compact THz system based on an ultrafast Yb-doped fiber amplifier," Optics Express, vol. 14, No. 17, (Aug. 21, 2006), pp. 7909-7913.

Chen, Q., et al., "Electro-optic transceivers for terahertz-wave applications," J. Optical Society of America B., vol. 18, No. 6 (Jun. 2001), pp. 823-831.

Rahman, Anis, "Electro-optic properties of dendrimer," J. Optical Society of America, (2007), 7 pages.

Gadret, G., et al., "Nonlinear Optical Properties of Poled Polymers," SPIE, Nonlinear Optical Properties of Organic Materials IV, vol. 1560 (1991), pp. 226-237.

Gordon, Daniel F., et al., "Tunable, high peak power terahertz radiation from optical rectification of a short modulated laser pulse," Optics Express, vol. 14, No. 15, (Jul. 24, 2006), pp. 6813-6822.

Hayden, Michael I., et al., New Materials for Optical Rectification and Electrooptic Sampling of Ultrashort Pulses in the Terahertz Regime, Journal of Polymer Science: Part B: Polymer Physics, vol. 41, (2003), pp. 2492-2500.

Herman, W.N. and Cline, J.A., "Chielectric relaxation: chromophore dynamics in an azo-dye-doped polymer," J. Optical Society of America B, vol. 15, No. 1, (Jan. 1998), pp. 351-358.

(56) References Cited

OTHER PUBLICATIONS

Website: http://spiedl.aip.org/getabs/servlet/GetabsServlet, Jen, Alex, K.Y., et al., "Highly efficient and thermally stable organic/polymeric electro-optic materials by dendritic approach," SPIE—The International Society for Optical Engineering, (2003 Copyright), 2 pages.

Michelotti, F., et al., "Study of the orientational relaxation dynamics in a nonlinear optical copolymer by means of a pole and probe technique," J. Appl. Physics, American Institute of Physics, vol. 80, No. 3, (Aug. 1, 1996), pp. 1773-1778.

Mortazavi, M.A., et al., "Second-harmonic generation and absorption studies of polymer-dye films oriented by corona-onset poling at elevated temperatures," J. Optical Society of America B, vol. 6, No. 4, (Apr. 1989), pp. 733-741.

Otomo, Akira, et al., "Remarkable optical properties of dendrimers for laser applications," Linear and Nonlinear Optics of Organic Materials, Proceedings of SPIE, vol. 4461, (2001), pp. 180-187.

Rahman, K.M.A., et al., "Adsorption of Poly(amidoamine) Dendrimers on Gold," American Chemical Society, Langmuir, vol. 16, No. 26, (2000), pp. 10154-10160.

Website: http://www.sciencedirect.com/science, Ramian, Gerald, "Nuclear Instruments and Methods in Physics Research Section A: Accelerators, Spectrometers, Detectors and Associated Equipment: The new UCSB free-electron lasers," ScienceDirect, vol. 318, Issues 1-3 (Jul. 1, 1992), pp. 225-229 (2 pages).

Reid, Matthew and Fedosejevs, Robert, "Quantitative comparison of terahertz emission from (100) InAs surfaces and a GaAs large-aperture photoconductive switch at high fluences," Applied Optics, vol. 44, No. 1 (Jan. 1, 2005), pp. 149-153.

Ricci, Vincent and Stegeman, George, I, "Poling of multilayer polymer films for modal dispersion phase matching of second-harmonic generation: effects of glass-transition temperature matching in different layers," J. Optical Society of America B, vol. 17, No. 8, (Aug. 2000), pp. 1349-1353.

Schildkraut, Jay S., "Limitations to the determination of the optical properties of a thin film by combined ellipsometric and surface plasmon resonance measurements," Applied Optics, vol. 27, No. 16, (Aug. 15, 1988), pp. 3329-3333.

Sinyukov, Alexander M. and Hayden, Michael L., "Generation and detection of terahertz radiation with multilayered electro-optic polymer films," Optics Letters, vol. 27, No. 1 (Jan. 1, 2002), pp. 55-57.

Sinyukov, Alexander M., et al., "Resonance enhanced THz generation in electro-optic polymers near the absorption maximum," Applied Physics Letters, vol. 85, No. 24 (Dec. 13, 2004), pp. 5827-5829.

Stuart, R.A., et al., "Present Status of the Compact EM THz Source," 3rd EMRS DTC Technical Conference, Edinburgh (2006), 6 pages.

Teng, C.C. and Man, H.T., "Simple reflection technique for measuring the electro-optic coefficient of poled polymers," Applied Physics Letters, vol. 56, No. 18 (Apr. 1990), pp. 1734-1736.

Xu, J.Z. and Zhang, X.C., "Optical rectification in an area with a diameter comparable to or smaller than the center wavelength of terahertz radiation," Optics Letters, vol. 27, No. 12, (Jun. 15, 2002), pp. 1067-1069.

Website: http://scitation.aip.org/getabs/servlet/GetabesServlet, Yang, K.H., et al., "Generation of Far-Infrared Radiation by Picosecond Light Pulses in $LiNbO3$," Applied Physics Letters, vol. 19, Issue 9 (Nov. 1, 1971), pp. 320-323 (2 pages).

Wang, Kanglin and Mittleman, Daniel M., "Metal wires for terahertz wave guiding," Nature, vol. 432, (Nov. 18, 2004), pp. 376-379.

Ma, Hong and Jen, Alex, K.Y., "Functional Dendrimers for Nonlinear Optics," Advanced Materials, vol. 13, No. 15, (Aug. 3, 2001), pp. 1201-1205.

\* cited by examiner 3400    3410

3415

3420

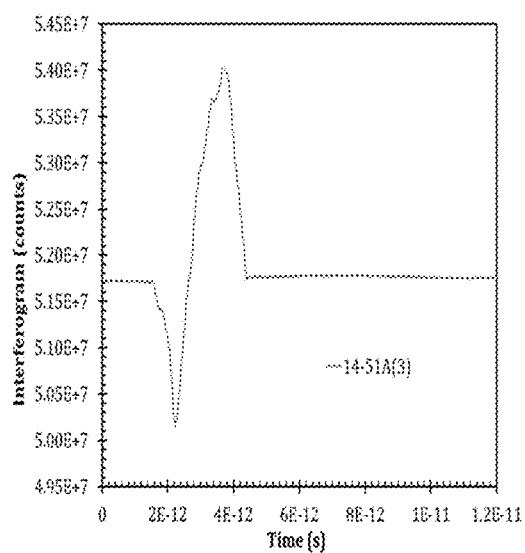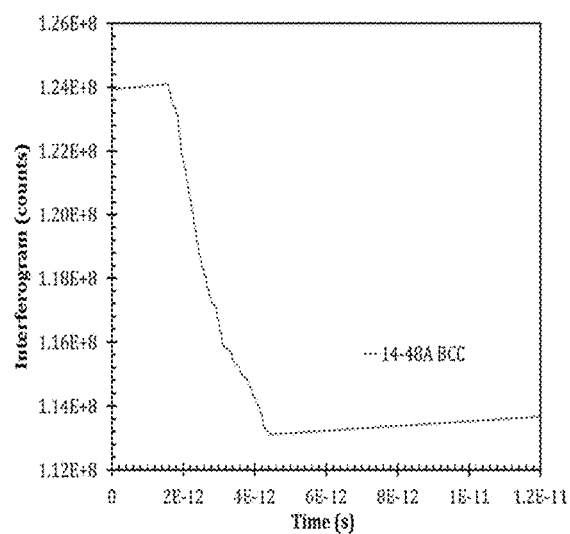
Figure 35A
Figure 35B

| | X | Y | Z | Component 1 | Component 2 | Component 3 | Component 4 |
|---|---|---|---|---|---|---|---|
| Row 1 | 38115.03762 | 16000 | 50000 | 8.600000381 | 533321.1846 | 8242017.578 | 4586582.391 |
| Row 2 | 38129.92044 | 16000 | 50000 | 8.600000381 | 540529.2626 | 8141587.003 | 4848551.865 |
| Row 3 | 38137.89762 | 16000 | 50000 | 8.600000381 | 545896.7553 | 8080097.483 | 4894712.394 |
| Row 4 | 38144.8985 | 16000 | 50000 | 8.600000381 | 550906.054 | 8102498.915 | 4737792.274 |
| Row 5 | 38151.87356 | 16000 | 50000 | 8.600000381 | 554325.6324 | 8090827.912 | 4767209.65 |
| Row 6 | 38158.78113 | 16000 | 50000 | 8.600000381 | 555844.1113 | 8164018.173 | 4786623.57 |
| Row 7 | 38165.75825 | 16000 | 50000 | 8.600000381 | 557252.8674 | 8189735.119 | 4792374.872 |
| Row 8 | 38171.759 | 16000 | 50000 | 8.600000381 | 555850.2896 | 8262897.858 | 4780312.783 |
| Row 9 | 38178.73606 | 16000 | 50000 | 8.600000381 | 553533.4541 | 8285240.927 | 4760387.216 |
| Row 10 | 38184.713 | 16000 | 50000 | 8.600000381 | 548893.0767 | 8380812.884 | 4720480.602 |
| Row 11 | 38191.71388 | 16000 | 50000 | 8.600000381 | 543088.9186 | 8496398.073 | 4670564.89 |
| Row 12 | 38198.8125 | 16000 | 50000 | 8.600000381 | 537778.4493 | 8609260.224 | 4624824.792 |
| Row 13 | 38204.59644 | 16000 | 50000 | 8.600000381 | 531854.884 | 8602633.409 | 4573952.285 |
| Row 14 | 38210.57338 | 16000 | 50000 | 8.600000381 | 526179.5097 | 8684795.279 | 4525143.084 |
| Row 15 | 38216.57412 | 16000 | 50000 | 8.600000381 | 520072.8317 | 8734674.692 | 4472626.551 |
| Row 16 | 38223.55113 | 16000 | 50000 | 8.600000381 | 513907.7971 | 8728047.877 | 4419607.251 |
| Row 17 | 38230.45681 | 16000 | 50000 | 8.600000381 | 506885.5212 | 8703123.244 | 4359215.876 |
| Row 18 | 38236.45756 | 16000 | 50000 | 8.600000381 | 501389.2427 | 8722271.637 | 4311947.878 |
| Row 19 | 38241.43437 | 16000 | 50000 | 8.600000381 | 488093.9865 | 8638841.819 | 4283806.734 |
| Row 20 | 38248.41144 | 16000 | 50000 | 8.600000381 | 481925.3688 | 8624215.004 | 4230558.392 |
| Row 21 | 38253.41296 | 16000 | 50000 | 8.600000381 | 488568.1793 | 8525367.058 | 4201686.451 |
| Row 22 | 38259.31756 | 16000 | 50000 | 8.600000381 | 484664.2977 | 8496248.812 | 4168113.145 |
| Row 23 | 38264.29437 | 16000 | 50000 | 8.600000381 | 481608.2789 | 8500442.425 | 4141831.365 |
| Row 24 | 38270.29512 | 16000 | 50000 | 8.600000381 | 480265.3959 | 8475317.792 | 4130282.508 |
| Row 25 | 38275.27194 | 16000 | 50000 | 8.600000381 | 478614.638 | 8411305.07 | 4116686.052 |
| Row 26 | 38281.27269 | 16000 | 50000 | 8.600000381 | 477757.3921 | 8303537.845 | 4108713.754 |

THICKNESS DETERMINATION AND LAYER CHARACTERIZATION USING TERAHERTZ SCANNING REFLECTOMETRY

CROSS REFERENCE TO RELATED APPLICATIONS

This application claims the benefit of U.S. Provisional Application No. 62/022,334, filed Jul. 9, 2014, U.S. Provisional Application No. 62/022,906, filed Jul. 10, 2014, and is a continuation-in-part of U.S. patent application Ser. No. 13/281,230, filed Oct. 25, 2011, which is a divisional of U.S. patent application Ser. No. 11/862,474, filed Sep. 27, 2007, which issued as U.S. Pat. No. 8,050,531 on Nov. 1, 2011, which claims the benefit of U.S. Provisional Application No. 60/827,206, entitled "Electro-Optic Dendrimer, Electro-Optic Sensor, THz Waveguide, and Production Thereof," filed Sep. 27, 2006 and is continuation-in-part of U.S. patent application Ser. No. 14/144,155, filed Dec. 30, 2013, which is a continuation of U.S. patent application Ser. No. 13/423,032, filed Mar. 16, 2012, which issued as U.S. Pat. No. 8,620,132 on Dec. 31, 2013, which claims the benefit of U.S. Provisional Application No. 61/454,157, filed Mar. 18, 2011, and which is a continuation-in-part of U.S. patent application Ser. No. 13/281,230, filed Oct. 25, 2011, which is a divisional of U.S. patent application Ser. No. 11/862,474, filed Sep. 27, 2007, which issued as U.S. Pat. No. 8,050,531 on Nov. 1, 2011, which claims the benefit of U.S. Provisional Application No. 60/827,206, entitled "Electro-Optic Dendrimer, Electro-Optic Sensor, THz Waveguide, and Production Thereof," filed Sep. 27, 2006; and U.S. patent application Ser. No. 13/423,032, which is a continuation-in-part of U.S. patent application Ser. No. 12/322,662, filed Feb. 5, 2009, which issued as U.S. Pat. No. 8,759,778 on Jun. 24, 2014, which claims the benefit of U.S. Provisional Application No. 61/026,233, filed Feb. 5, 2008, entitled "Terahertz Time Domain and Frequency Domain Spectroscopy" and is a continuation-in-part of U.S. patent application Ser. No. 11/862,473, filed Sep. 27, 2007, which issued as U.S. Pat. No. 7,919,755 on Apr. 5, 2011, entitled "Dendrimer Based Electro-optic Sensor", and U.S. patent application Ser. No. 11/862,474, filed Sep. 27, 2007, which issued as U.S. Pat. No. 8,050,531 on Nov. 1, 2011, entitled "Dendrimer Based Terahertz Generator", all of which are herein incorporated by reference in their entireties. This application is related to U.S. patent application Ser. No. 11/862,473, entitled "Dendrimer Based Electro-Optic Sensor", filed on Sep. 27, 2007, which issued as U.S. Pat. No. 7,919,755 on Apr. 5, 2011; U.S. patent application Ser. No. 10/710,303, filed Jul. 1, 2004, which issued as U.S. Pat. No. 7,389,029 on Jun. 17, 2008; U.S. patent application Ser. No. 11/335,110, filed on Jan. 19, 2006, which issued as U.S. Pat. No. 7,412,121 on Aug. 12, 2008; and U.S. patent application Ser. No. 10/605,638, filed on Oct. 15, 2003, which issued as U.S. Pat. No. 7,110,627 on Sep. 19, 2006, all of which are herein incorporated by reference.

FIELD OF INVENTION

This application is related to terahertz reflectometry.

BACKGROUND

The recently accessible terahertz (THz) portion of the electromagnetic spectra, also known as T-ray spectra, has a wide potential to be employed in materials, medical, biomedical, and biological studies and characterization.

SUMMARY

A terahertz scanning reflectometer system is described herein for in-situ measurement of polymer coating thickness and semiconductor wafers inspection for sub-surface defects in a non-destructive and non-invasive fashion.

BRIEF DESCRIPTION OF THE DRAWINGS

A more detailed understanding may be had from the following description, given by way of example in conjunction with the accompanying drawings wherein:

FIGS. 35A and 35B show time-domain signal (interferogram) of benign skin sample (7A) and BCC biopsy sample (7B);

FIG. 38 shows a sample of the data collected for 3D imaging;

DETAILED DESCRIPTION

A high sensitivity terahertz scanning reflectometer (TSR) is used to determine the thickness of multiple layers, layer characterization and surface characterization.

The TSR uses a continuous wave (CW) terahertz source that generates broadband terahertz radiation from an electro-optic dendrimer as disclosed, for example, in U.S. patent application Ser. No. 14/144,155, filed Dec. 30, 2013, which is a continuation of U.S. patent application Ser. No. 13/423,032, filed Mar. 16, 2012, which is a continuation of U.S. patent application Ser. No. 13/423,032, filed Mar. 16, 2012, which claims the benefit of U.S. Provisional Application No. 61/454,157, filed Mar. 18, 2011, the contents of which are hereby incorporated by reference herein and is a continuation-in-part of U.S. patent application Ser. No. 13/281,230, filed Oct. 25, 2011, which is a divisional of U.S. patent application Ser. No. 11/862,474, filed Sep. 27, 2007, which issued as U.S. Pat. No. 8,050,531 on Nov. 1, 2011, which claims the benefit of U.S. Provisional Application No. 60/827,206, entitled "Electro-Optic Dendrimer, Electro-Optic Sensor, THz Waveguide, and Production Thereof," filed Sep. 27, 2006; and a continuation-in-part of U.S. patent application Ser. No. 12/322,662, filed Feb. 5, 2009, which claims the benefit of U.S. Provisional Application No. 61/026,233, filed Feb. 5, 2008, entitled "Terahertz Time Domain and Frequency Domain Spectroscopy" and is a continuation-in-part of U.S. patent application Ser. No. 11/862,473, filed Sep. 27, 2007, which issued as U.S. Pat. No. 7,919,755 on Apr. 5, 2011, entitled "Dendrimer Based Electro-optic Sensor", and U.S. patent application Ser. No. 11/862,474, filed Sep. 27, 2007, which issued as U.S. Pat. No. 8,050,531 on Nov. 1, 2011, entitled "Dendrimer Based Terahertz Generator", all of which are herein incorporated in their entireties. This application is related to U.S. patent application Ser. No. 11/862,473, entitled "Dendrimer Based Electro-Optic Sensor", filed on Sep. 27, 2007, which issued as U.S. Pat. No. 7,919,755 on Apr. 5, 2011; U.S. patent application Ser. No. 10/710,303, filed Jul. 1, 2004, which issued as U.S. Pat. No. 7,389,029 on Jun. 17, 2008; U.S. patent application Ser. No. 11/335,110, filed on Jan. 19, 2006, which issued as U.S. Pat. No. 7,412,121 on Aug. 12, 2008; and U.S. patent application Ser. No. 10/605,638, filed on Oct. 15, 2003, which issued as U.S. Pat. No. 7,110,627 on Sep. 19, 2006, all of which are herein incorporated by reference, all of which are herein incorporated in their entireties.

Figure 1:
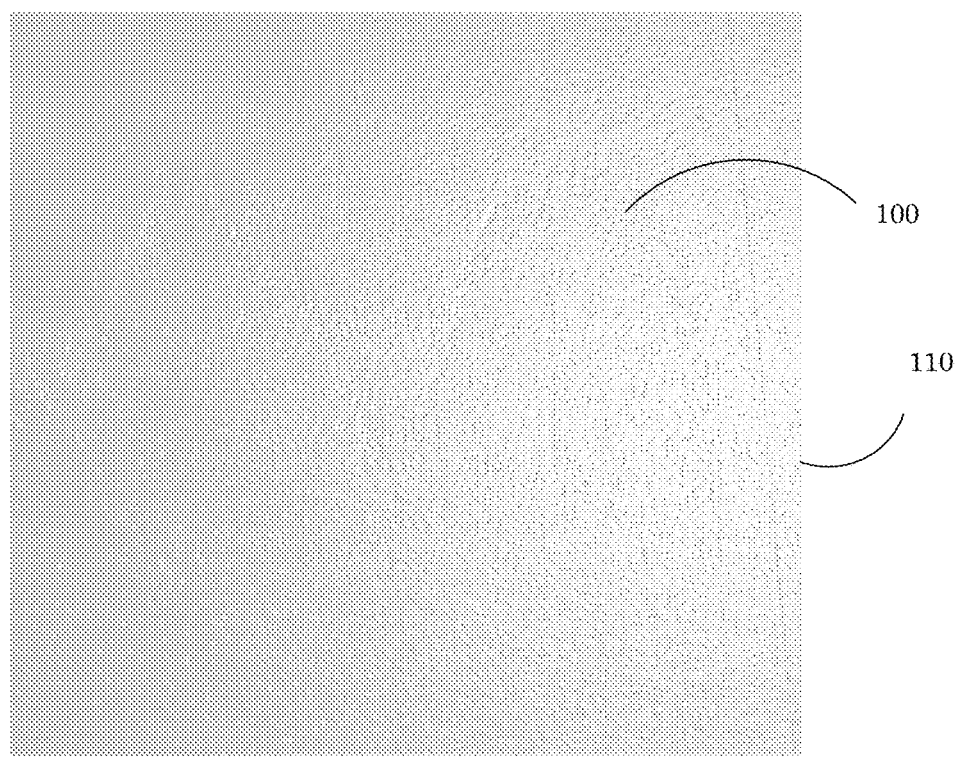
FIG. 1 shows a polymer coated surface of an as received wooden panel.

Described herein is a two-beam scanning reflectometry for in-situ measurement of polymer coating thickness. FIG. 1 shows a polymer coated surface 100 of an as received wooden panel 110.

Figure 2:
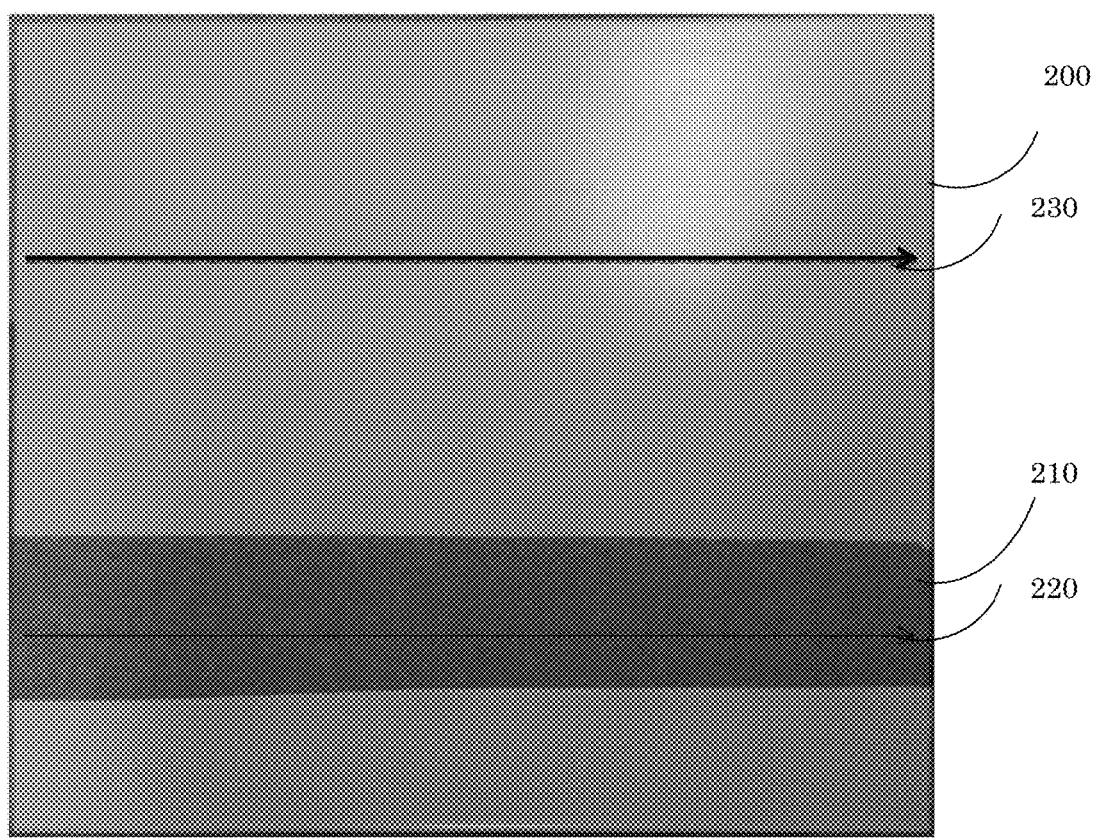
FIG. 2 shows that a strip of coating was removed from the panel to expose the wooden substrate.

FIG. 2 shows a panel 200 of FIG. 1 with a strip of coating removed from the panel to expose a wooden substrate 210. In addition, FIG. 2 illustrates the principle of two-beam scanning reflectometry for in-situ thickness measurement. As stated, a strip of paint was removed from the panel 200 to expose the wooden substrate 210. Two different beams are used simultaneously to scan the panel: 1) a first beam 220 follows the exposed substrate (thin line) and a second beam 230 follows the polymer coating (thick line). Assuming the physical properties remain unchanged during scanning, differences in the intensities or the reflected powers between the two beams are used to compute the thickness of the polymer coating based on prior calibration.

Figure 3:
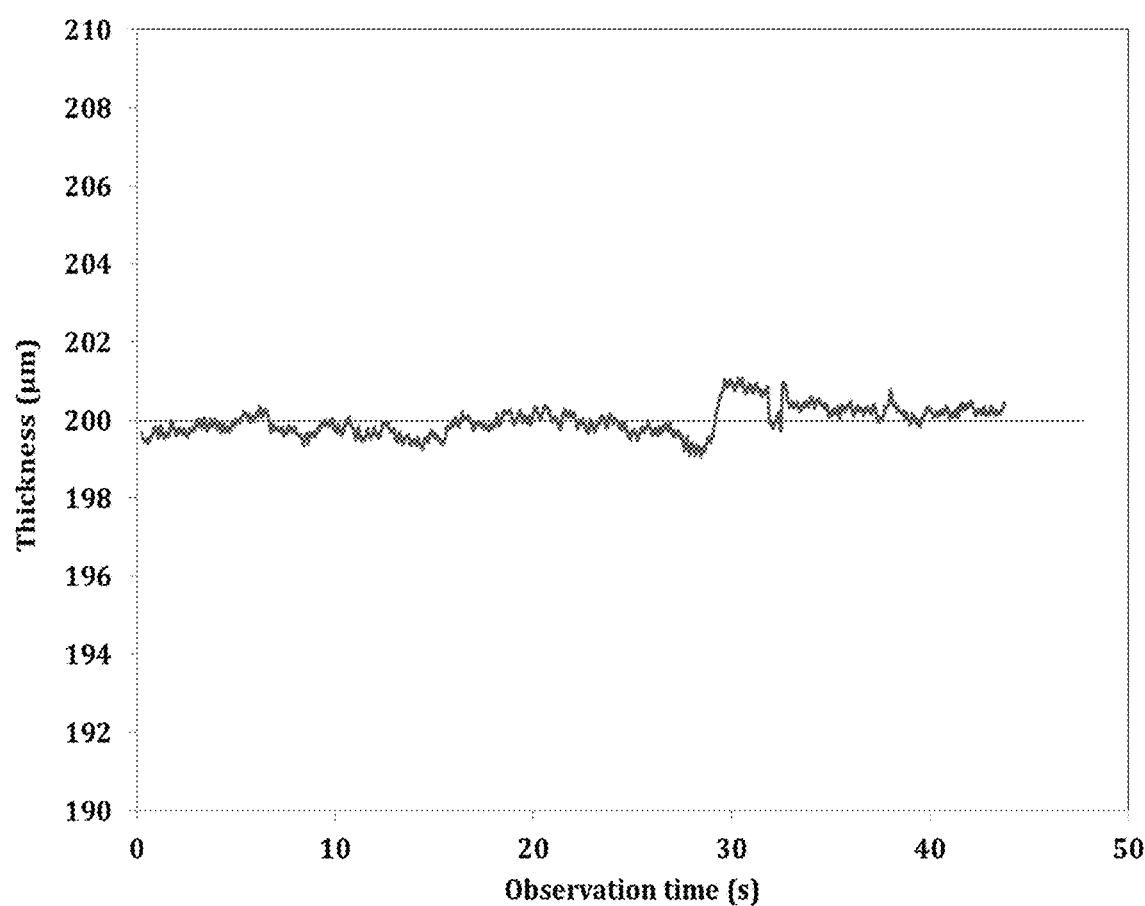
FIG. 3 shows a calibration of a system for a known coating thickness of 200 µm.

FIG. 3 shows a calibration plot of a system for a known coating thickness of 200 µm. In particular, shown is a calibration of a system for 200 µm thick polymer film on a wood substrate.

Figure 4:
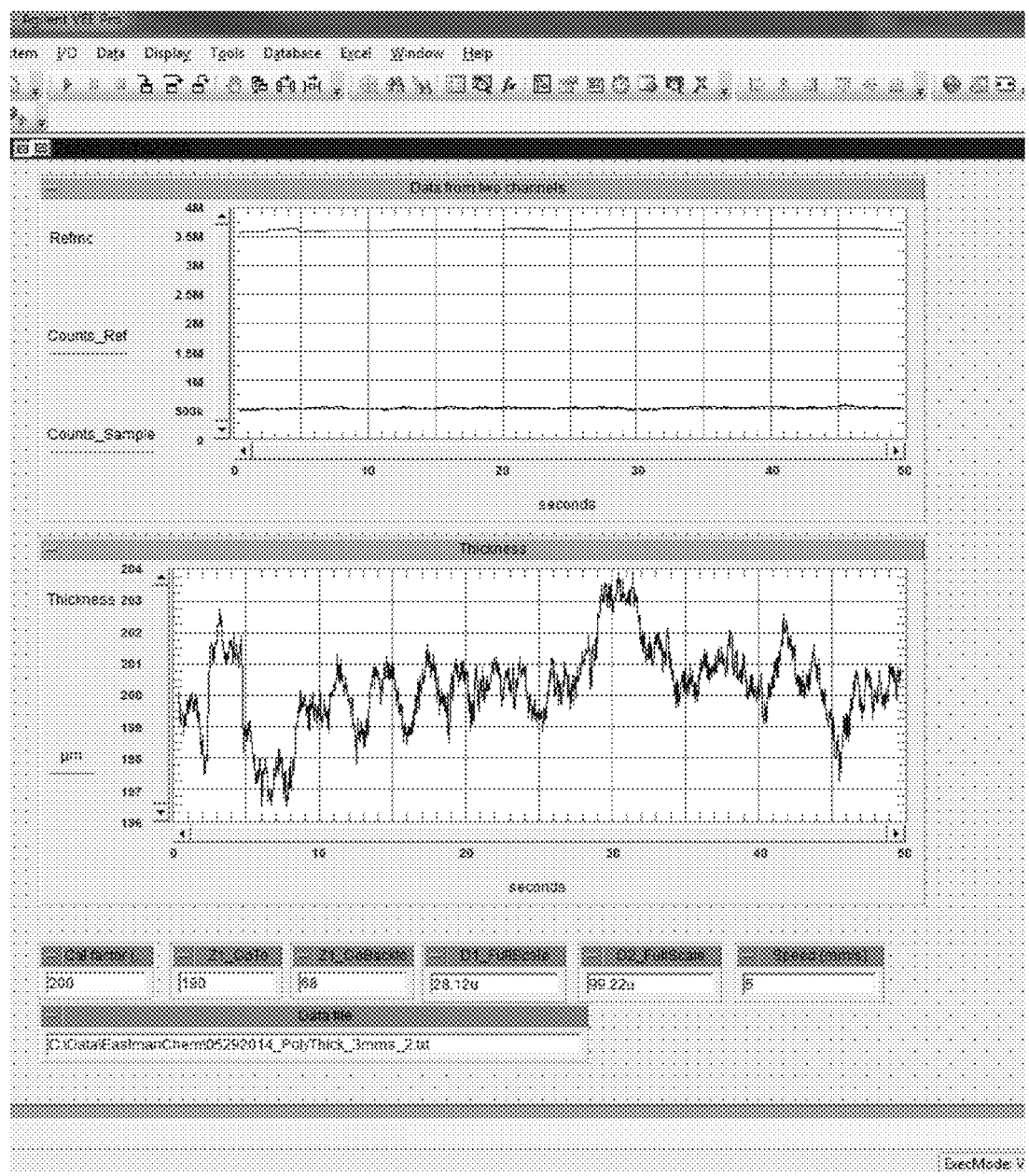
FIG. 4 shows the measurement console for in-situ thickness monitoring.

FIG. 4 shows a console for the in-situ thickness measurement by a two-beam scanning reflectometry. Here the calibration factor was entered from prior calibration. Other parameters for continuous scanning may be entered from this console. Thickness data are plotted graphically and also stored in a data file. As discussed herein below, a top plot of the console shows the difference between traces of a reference beam and a scanning beam and a bottom plot shows the actual thickness. Total scanning length is 125 mm.

FIG. 4 shows the measurement console for thickness monitoring. Here a wooden panel was mounted on an automated stage and the sample was scanned at a speed between 5 mm/s and 10 mm/s. Total scanning length was 125 mm. Thickness data are plotted graphically and also stored in a data file for further analysis. The top plot of the console (FIG. 4) shows the difference between the traces of the reference beam and the scanning beam. The bottom plot shows the calculated thickness. As seen from FIG. 4, the error in measurements is within ±4 µm. FIG. 4 also shows that the polymer coating is more or less uniform within the error limit of ±4 µm.

Figure 5:
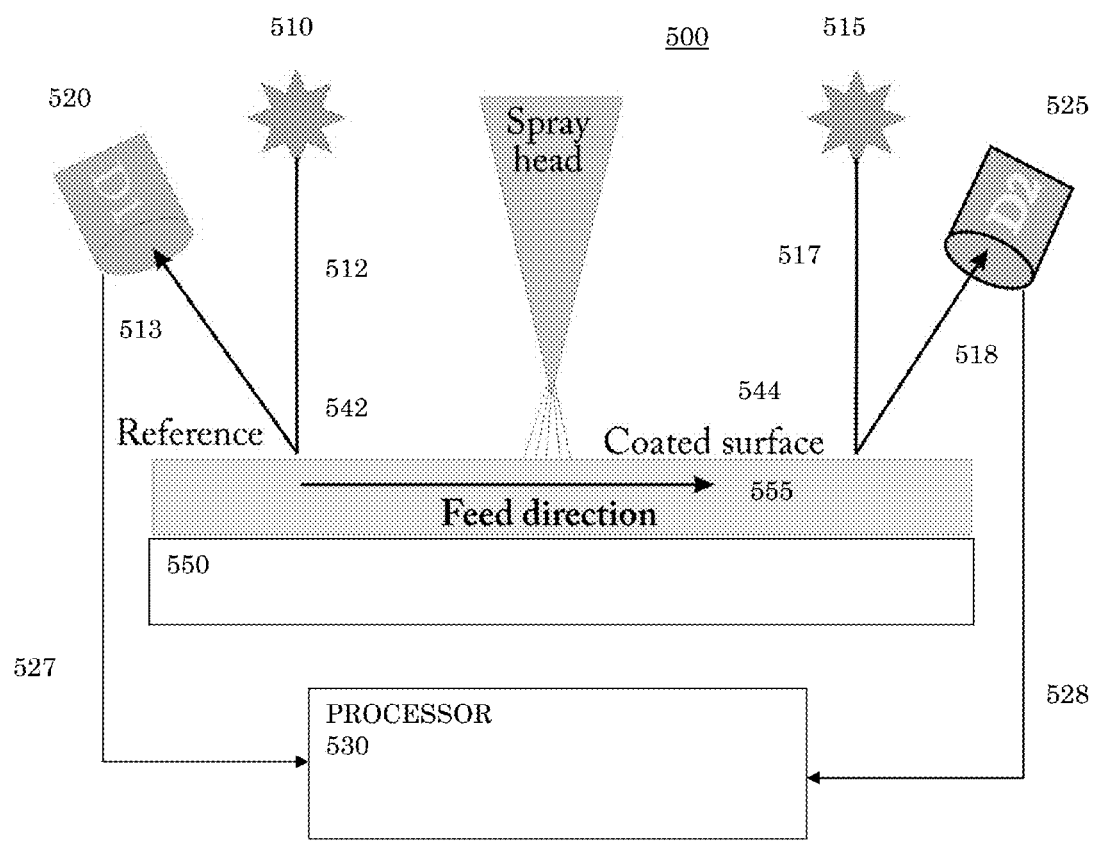
FIG. 5 shows a system for two beam scanning reflectometry.

FIG. 5 shows an embodiment of a system and method for coating thickness determination by two-beam scanning reflectometry. A two-beam scanning reflectometry system 500 includes a first continuous wave terahertz source 510, a second continuous wave terahertz source 515, a first detector 520, a second detector 525 and a processor 530. A panel 540 is positioned on an automated stage, mount or motorized mechanism 550, which moves the panel 540 in a feed direction 555. A spray head 560 coats the panel 540 as the panel 540 is moved by the motorized mechanism 550 in the feed direction 555.

The first continuous wave terahertz source 510 is configured to generate terahertz radiation 512 toward a reference layer 542 and the second continuous wave terahertz source 515 is configured to generate terahertz radiation 517 toward a target layer 544, which is now a coated surface. The first detector 520 is configured to detect a reference layer reflected beam 513 and the second detector 525 is configured to detect a target layer reflected beam 518. The processor 530 is configured to receive information and/or signals 527 and 528 from detectors 520 and 525 to determine a difference between the reflected intensities or powers of the reference layer reflected beam 513 and target layer reflected beam 518.

As outlined in FIG. 5, two-beam reflectometry may be effectively utilized for monitoring the polymer coating thickness with prior calibration for each polymer. A model derived from the a priori calibration, is then utilized to compute the thickness in-situ, based on the difference of the reference and the probing beams. This principle may be expanded for monitoring multiple layers by adding one more beam per layer. The model must be worked out for each polymer-substrate combinations separately.

Figure 6:
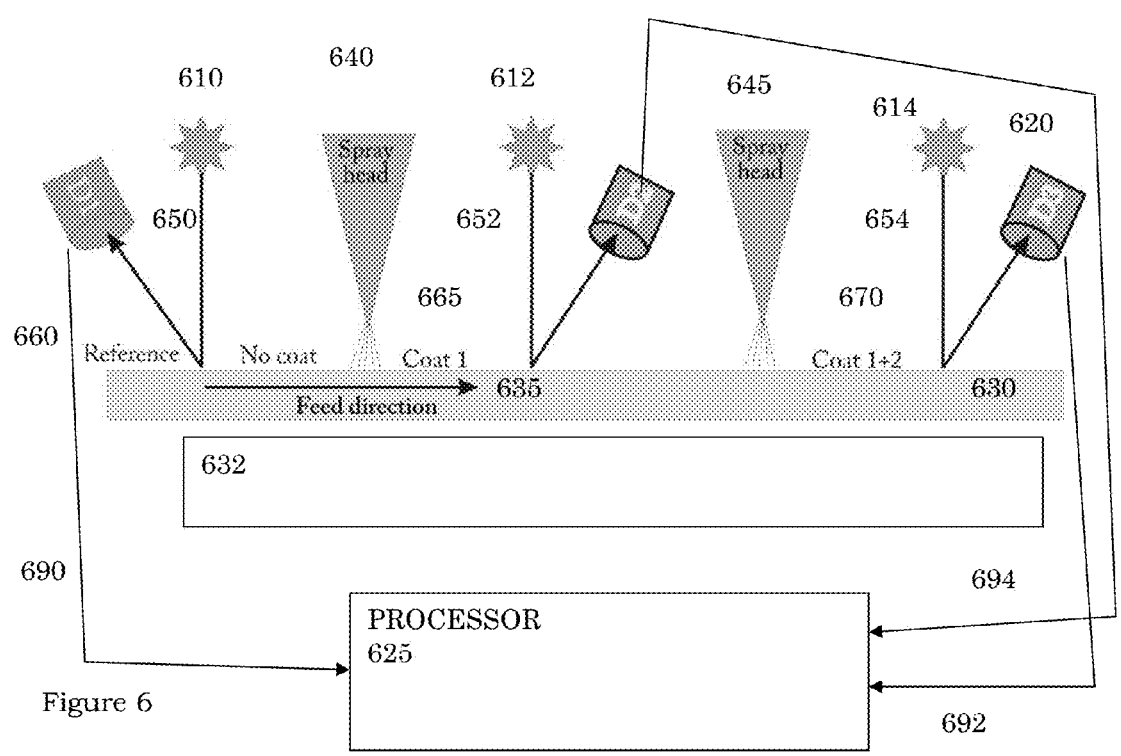
FIG. 6 shows a system for multiple beam scanning reflectometry.

FIG. 6 shows an embodiment of a system and method for multi-beam scanning reflectometry for determination of thicknesses of different layers in-situ. A multi-beam scanning reflectometry system 600 includes a first continuous wave terahertz source 610, a second continuous wave terahertz source 612, a third continuous wave terahertz source 614, a first detector 616, a second detector 618, a third detector 620 and a processor 625. A panel 630 is positioned on an automated stage, mount or motorized mechanism 632, which moves the panel 630 in a feed direction 635. A spray head 640 coats the panel 630 with a first coat as the panel 630 is moved by the motorized mechanism 632 in the feed direction 635. A second spray head 645 adds a second coat onto the first coat as the panel 630 is moved further along in the feed direction 635.

The first continuous wave terahertz source 610 is configured to generate terahertz radiation 650 toward a reference layer 660, the second continuous wave terahertz source 612 is configured to generate terahertz radiation 652 toward a first coated layer 665, and the continuous wave terahertz source 614 is configured to generate terahertz radiation 654 toward a first+second coated layer 670. The first detector 616 is configured to detect a reference layer reflected beam 680, the second detector 618 is configured to detect a first coated layer reflected beam 682 and the third detector 620 is configured to detect a first+second coated layer reflected beam 684. The processor 625 is configured to receive information and/or signals 690, 692 and 694 from detectors 616, 618, and 620 to determine a difference between the intensities or the reflected powers of the reference layer reflected beam 680 and first coated layer reflected beam 682 and a difference between the first coated layer reflected beam 682 and the first+second coated layer reflected beam 684.

As outlined in FIG. 6, a sequential difference between successive detectors is utilized to measure the thickness of the respective layers. For example, the difference between detectors 616 and 618 will be utilized to compute the thickness of the first coated layer 665 per prior calibration. Similarly, the difference between detectors 618 and 620 will be utilized to determine the thickness of a second coat based on a priori calibration. In a similar fashion, additional coats or layers may be measured using additional sources and detectors.

Figure 7:
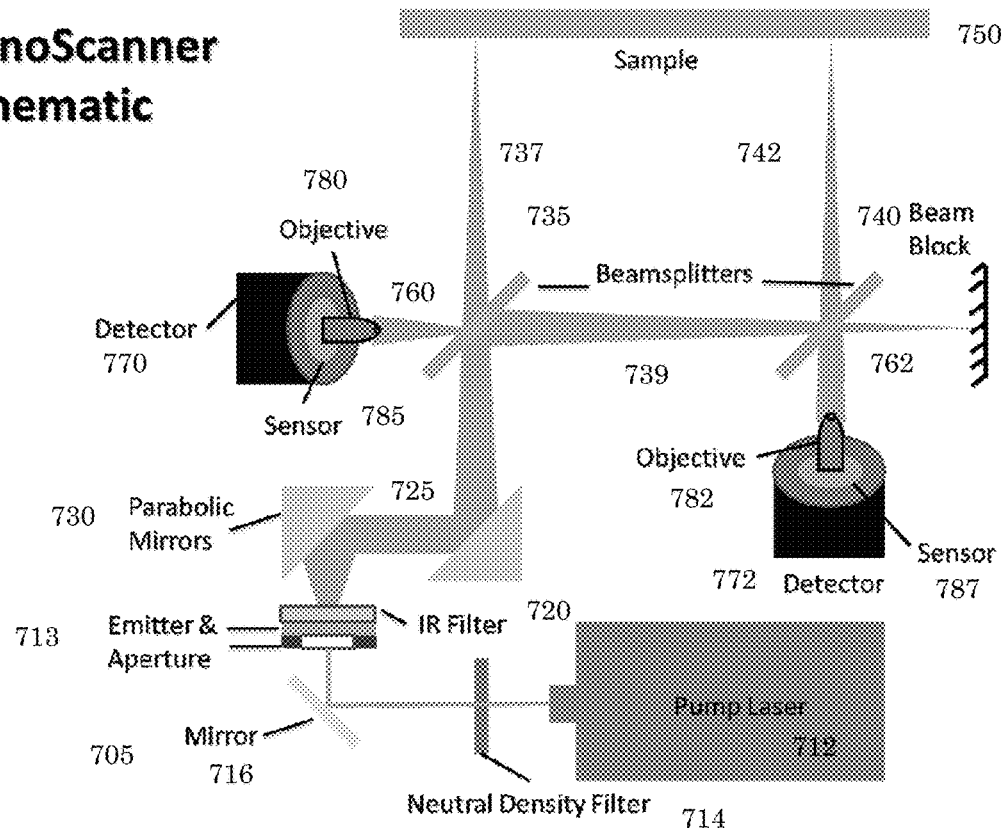
FIG. 7 illustrates an example nanoscanner.

FIG. 7 shows an embodiment of an example two-beam scanning reflectometer or nanoscanner 700 that may be used as a two-beam scanning reflectometer. The two-beam scanning reflectometer 700 includes a terahertz generator 705 comprising a pump laser 712, a neutral density filter 714, a mirror 716, an emitter and aperture 718 and an IR filter 720. An emitted terahertz beam 725 is deflected using parabolic mirrors 730 to a beamsplitter 735 which directs one beam 737 to a sample 750 and another beam 739 to another beamsplitter 740, which in turn directs another beam 742 to the sample 750. The reflected beams 760 and 7562 are detected by a first detector 770 and a second detector 772, respectively. Each detector 770 and 772 has an objective 780,782 and sensor 785,787, respectively.

Figure 8:
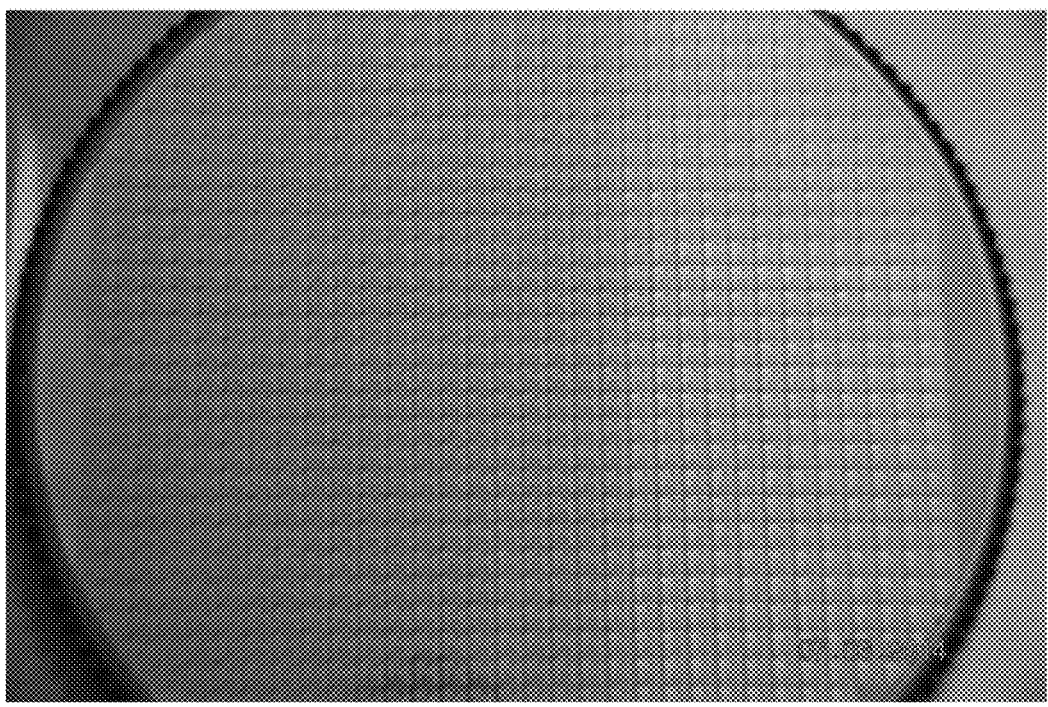
FIG. 8 shows example intricate patterns on a semiconductor wafer.
Figure 9:
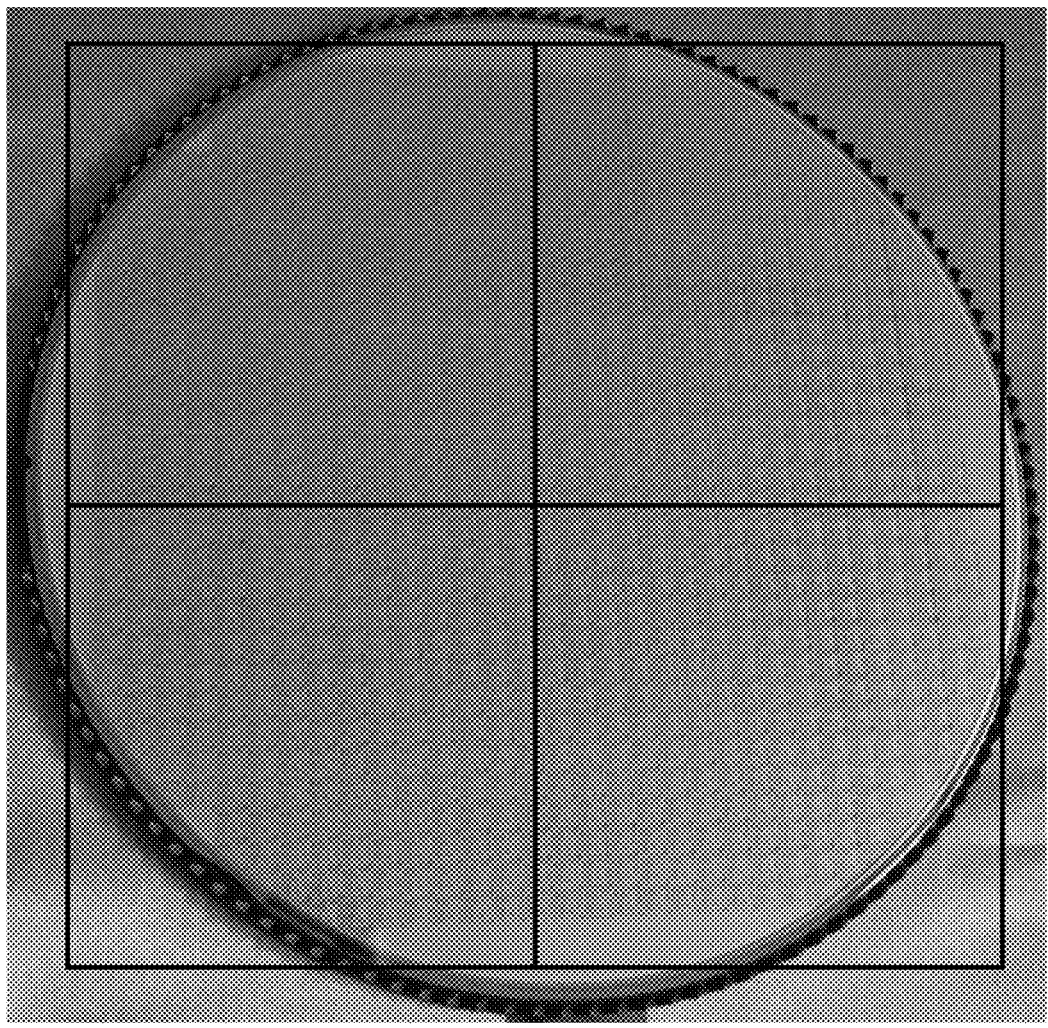
FIG. 9 shows example 4 quadrants of a semiconductor wafer.

Described herein is a method using, for example, a reflectometer as shown in FIG. 7 with one beam or multiple beams, with sub-surface imaging for effective characterization of various aspects of semiconductor wafer testing. An example wafer is shown in FIG. 8, which shows example intricate patterns on a semiconductor wafer. Each rectangle represents an individual integrated circuit (or a die). A single defective die may cause the whole wafer to be rejected. In an embodiment, a wafer may be divided up into four quadrants as shown in FIG. 9, where each quadrant has a detector as described herein. Additionally, more quadrants may be defined by adding more detectors for further speeding up the inspection process. For example, an 8 or 16 detector array will reduce the time by a factor of 8 or 16 times.

Figure 10:
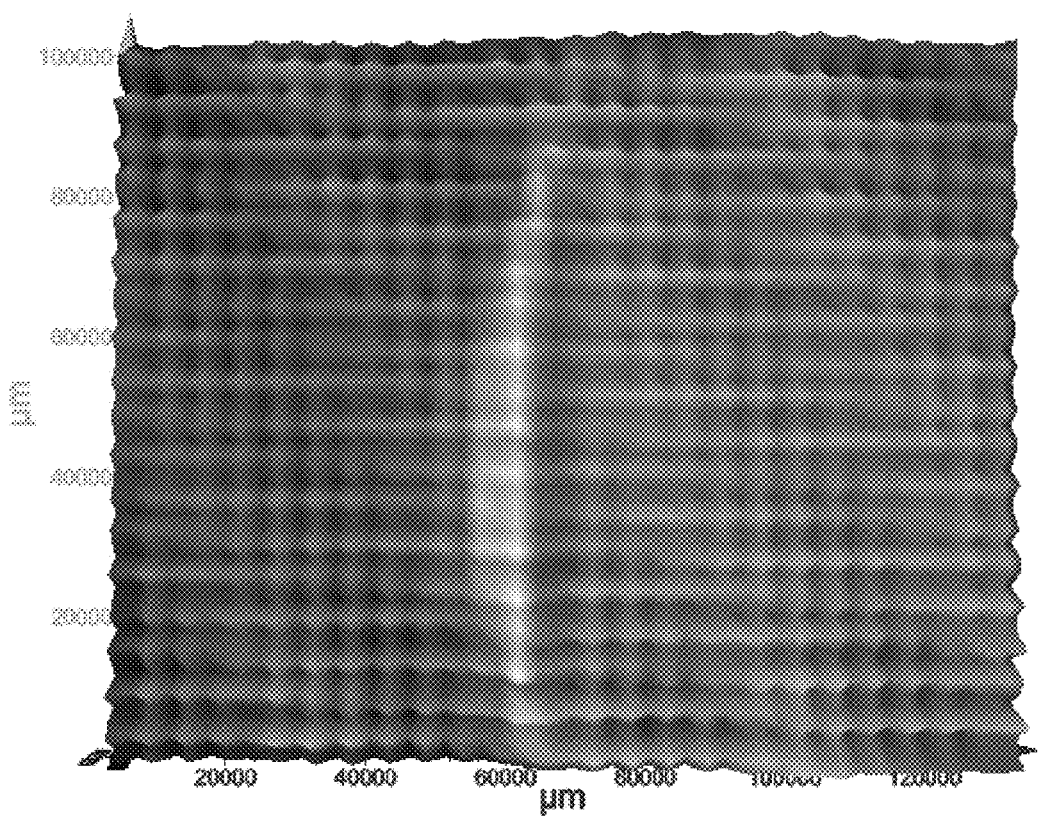
FIG. 10 shows a reconstructed surface image of a segment of the wafer that shows significant discrepancy causing the wafer to reject.

Exemplary results of scanning a wafer can be analyzed for defect determination. For example, FIG. 10 shows a reconstructed surface image of a segment of the wafer that shows significant discrepancy causing the wafer to reject. A layer-by-layer inspection from the beginning of the process would pin point the origin the discrepancy thus helping to avoid such rejects. In another embodiment, terahertz reflectometry may be used for controlling wafer polishing for planarization via high precision thickness monitoring. In another embodiment, terahertz spectrometry is used to identify self-assembled monolayer (SAM) on a wafer.

The embodiments described herein may be extended to other substrates transparent to terahertz radiation. For example, the system may be used for characterizing different SAM coated silicon wafers for identifying two different SAM species. The Fourier transform absorbance spectra of both SAM specimens reveals several distinguishable absorbance peaks that may be used as signatures of the respective SAMs. The SAM having 18 carbon chain exhibits higher absorbance than that of the SAM comprised of 8 carbon chain. This is consistent with the higher molecular weight of the former.

Terahertz spectrometry and reflectometry systems provide effective solutions for wafer reject minimization by means of sub-surface, nanoscale, 3D imaging, via a non-destructive and non-contact route. For example, a terahertz sub-surface 3D imager may be used, which is described in Effective Testing For Wafer Reject Minimization by Terahertz Analysis and Sub-surface Imaging, ASMC Publication, 2014, the contents of which are herein incorporated by reference in its entirety. Simultaneous reflection and transmission measurements allow inspection of semiconductor wafers during fab processes (in-situ) as well as for post-fab characterizations (ex-situ). The intensity of the reflected terahertz beam is proportional to the specific features (layers) of the specimen under test. Therefore, measured intensity may be modeled in terms of suitable physical parameters such as refractive index, density, dielectric constant, etc., via a modified Beer-Lambert's law. For a given wafer, all material parameters remain unchanged during measurements, because, terahertz radiation is non-ionizing and does not perturb the intrinsic properties. Thus, the reflectance, R, is proportional to the variations in materials at the point where the beam is incident. As such, the reflectance is dependent on the spatial and angular coordinates: R (x, y, z, θ).

A 3D reconstructed image generated from reflectance, therefore, will yield the characteristic features (patterns) on the substrate, see for example, FIG. 10. Another advantage of the terahertz scanner is that silicon and other semiconductor wafers are transparent at these wavelengths. Therefore, scanning may be done across the thickness of a wafer for inspecting internal layers. So, if there is a hole or void on the substrate or in any of the sub-surface layers, that will be identifiable from both reflected and transmitted intensities. Based on the above principle, a signature of a given defect may be established. Any defect such as, inclusions, cracks, non-uniformity, or particulate foreign material can be detected and identified by this technique.

Figure 11:
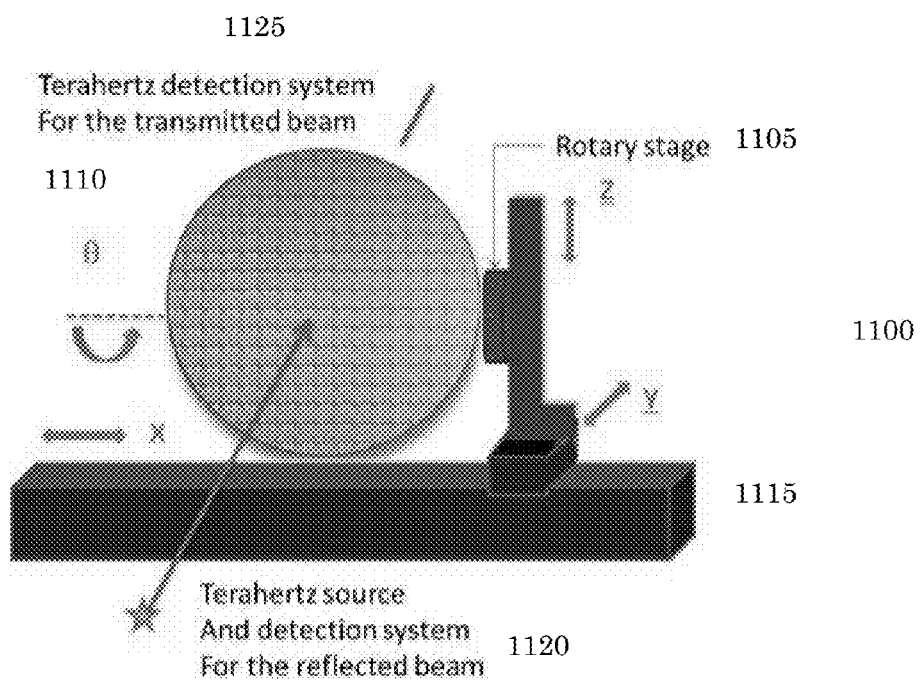
FIG. 11 is a nanoscanner arrangement in accordance with an embodiment.

Moreover, defect size may be estimated from either a 2-D scan, or 3-D scanned reconstructed imaging. The terahertz nanoscanner 1100, as shown in FIG. 11, deploys a non-contact measurement system with an adjustable stand-off distance. The sample space is adjustable to accommodate required sample size. A rotary stage 1105 having a rotary axis enables examination of a wafer 1110 (or other sample) from different viewing angles. This is important because cracks or other non-uniformities might not be along a straight line-of-sight. Thus an angular scan enables viewing hidden features. In addition, with the advent of the angular axis, one can scan cylindrical objects in a conformal fashion.

Another important issue for the semiconductor wafers is the requirement of planarization as the fabrication process progresses with layer by layer deposition and patterning. Chemical and mechanical polishing (CMP) used for wafer planarization requires just sufficient material to be removed, but too much removal can result in failure/rejection of the wafer. As such, precise thickness control, on the order of nanometers, is required for lowering the reject rate. Terahertz transmission and/or reflection measurements can be used for monitoring the CMP process. Described herein is a method for controlling the polishing process based on given thickness criterion. The removal of material from the wafer surface is a complex function of the polishing slurry, spin speed and duration, among other factors. However, a straightforward method that minimizes monitoring of individual variables is the direct measurement of the thickness of the wafer, from which the mass of the removed material may also be calculated. In this method a terahertz beam is reflected off of the polishing surface while a transmission measurement may also be carried out simultaneously. A requirement of this technique is a rigorous calibration of the material removal as a function of polishing conditions while all physical parameters essentially remain fixed. This process reduces the number of control variables to a single parameter, i.e., reflected (and/or transmitted) power vs. thickness removed.

Additionally, semiconductor wafers' surface needs to be modified for different chemistry in preparation of processes such as patterning of waveguides or CMOS process with different functionalities. Common surface modification involves making a wafer hydrophilic or if it is already hydrophilic, then converting it to hydrophobic. This is uniquely done by various self-assembled monolayers (SAMs). However, it is difficult to characterize the SAMs with common laboratory instruments (e.g., UV/Vis, Raman or FTIR), because, SAMs being an only one molecule thick layer, physical characterization between different SAMs applied on wafer surfaces is challenging. Terahertz spectroscopy offers an advent of characterizing the molecular systems—even with minimal structural and mass differences—owing to its ultra-high sensitivity stemmed from the fact that terahertz photons interact with the entire molecule as opposed to a bond or a charge states as used by its predecessors.

As shown herein, exemplary results of wafer scans have been analyzed for defect determination. Additionally, terahertz reflectometry for wafer polishing has been exemplified with data. Finally, application of terahertz spectrometry for identifying self-assembled monolayer (SAM) on a wafer is also outlined with an example.

Figure 12:
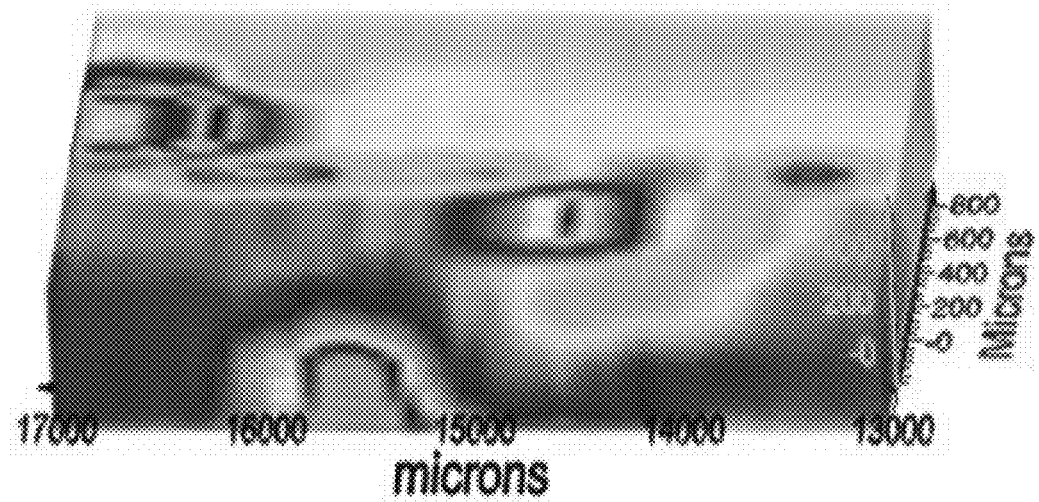
FIG. 12 is a 3D image of a wafer area.

FIG. 11 displays a schematic diagram of the terahertz nano-scanner 1100. The wafer 1110 is mounted on a rotary stage 1105 which is mounted on a XYZ stage 1115. The measurement system comprises of an electro-optic dendrimer based continuous wave (CW) terahertz source 1120 and a matching detection system 1125 as described herein. All positioning stages are automated; the linear stages have a resolution of ~25 nm. As shown in FIG. 11, this design is based on normal incidence of the terahertz beam to the target. In case of normal incidence, the incident beam is the sum of the reflected, transmitted, absorbed and scattered intensities. Assuming the material properties remain unchanged during measurement, the reflectance will be proportional to the material characteristics. Ordinarily, the Beer-Lambert's law is used to determine the concentration, C, of a solute in a solvent from absorbance data: $A = \in lC$, where l is the path length and $\in$ is the extinction coefficient (or molar absorptivity). Since the reflectance, R, is material dependent, a modified Beer-Lambert's law may be stated as, $$R(r) = \in(r), l(r), \rho(r), \quad \text{Equation (1)}$$

where, the reflectance is coordinate dependent because the materials on a wafer is position dependent, which in turn causes variation in the path length, l(r), and consequently variation in the coefficient ρ(r). It is notable that, the coefficient ρ(r) may be used for modeling desired material parameters such as density, dielectric constant, refractive index, etc. Obviously, this modeling gives the effective value of the chosen parameter as opposed to the complex quantity. Mapping of R(r) yields a 3D visualization of the specimen. FIG. 12 shows a 3D surface plot of a wafer where different features are depicted by different shading and their sizes are as indicated by the coordinates of the axes.

Figure 13A:
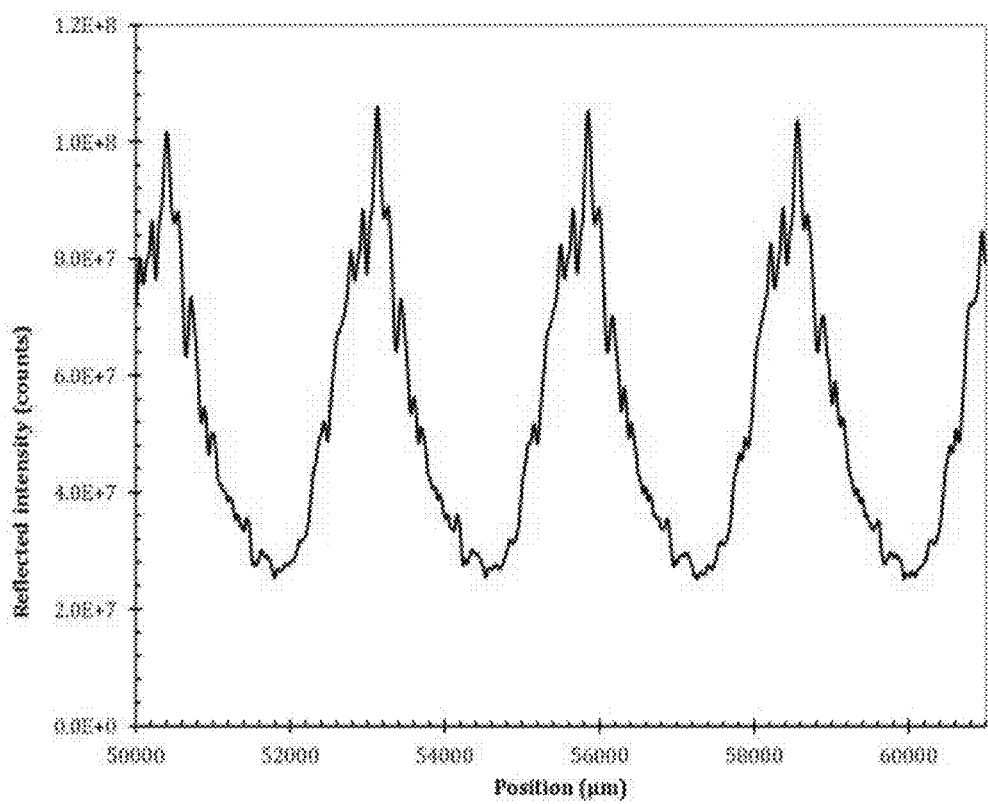
FIGS. 13A and 13B are high resolution scan patterns of a wafer.
Figure 13B:
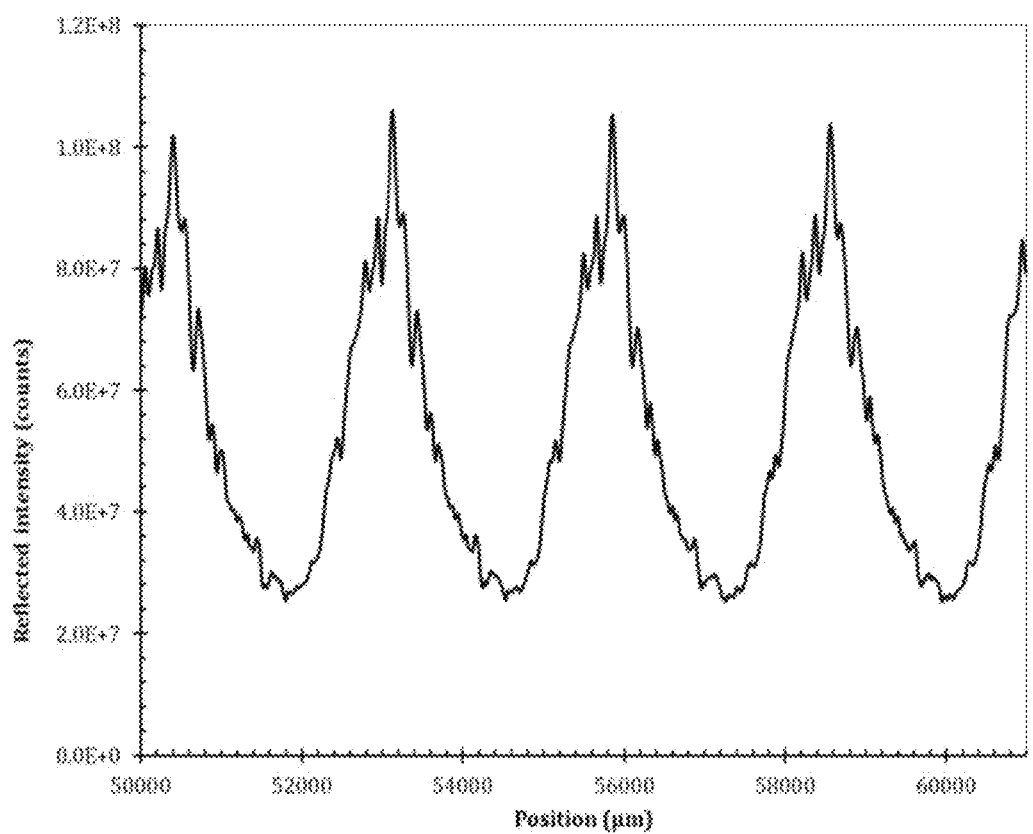
Figure 14:
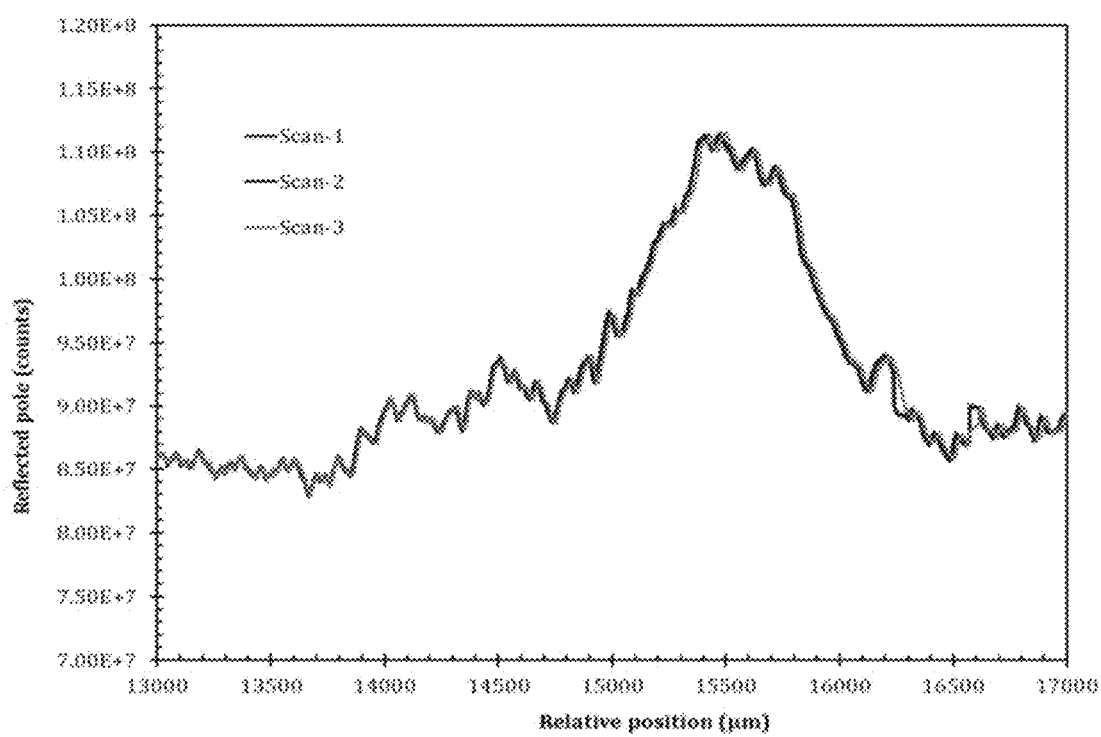
FIG. 14 is a plot of reproducibility of the traces.
Figure 15:
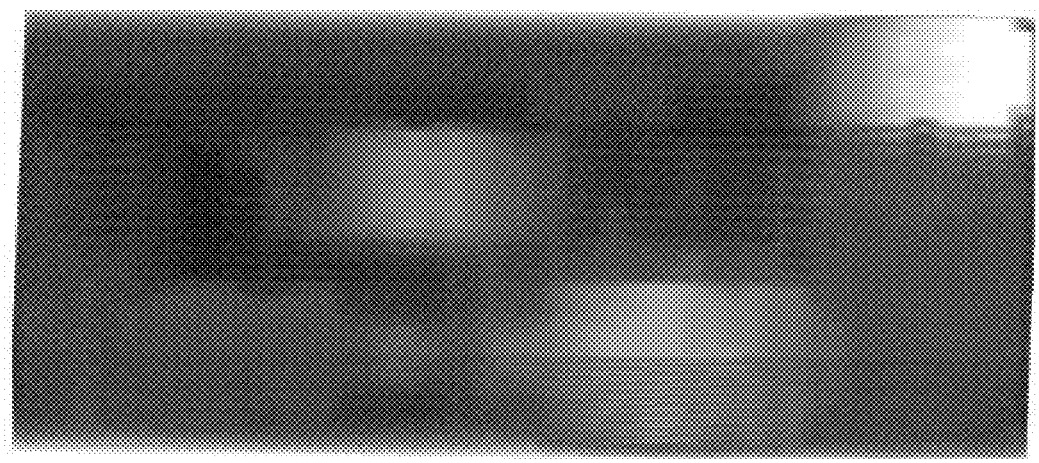
FIG. 15 is a reconstructed 3D representation of a problem area in a wafer.

FIGS. 13A and 13B show a pattern of adjacent dies on a wafer revealed by a 1D scan and also show that adjacent layers are detectable by their unique reflected intensity. A high resolution scan thus clearly shows the start, the end, and intricate pattern for each die on a wafer (FIG. 13B). The repetitive pattern from high resolution scan serves as a distinguishing metric for good dies from the bad ones. Since the scans are in exact coordinates, one can inspect the patterns closely for their irregularity and/or defect conditions. Once a defect position is identified, insight from process parameters may be used to deduce the actual nature of the defect. FIG. 14 shows the reproducibility of the measurements. FIG. 15 shows a reconstructed sub-surface image of an area; a comparison of such images between a good and a bad area will reveal the exact position and layer of the defect.

Figure 16:
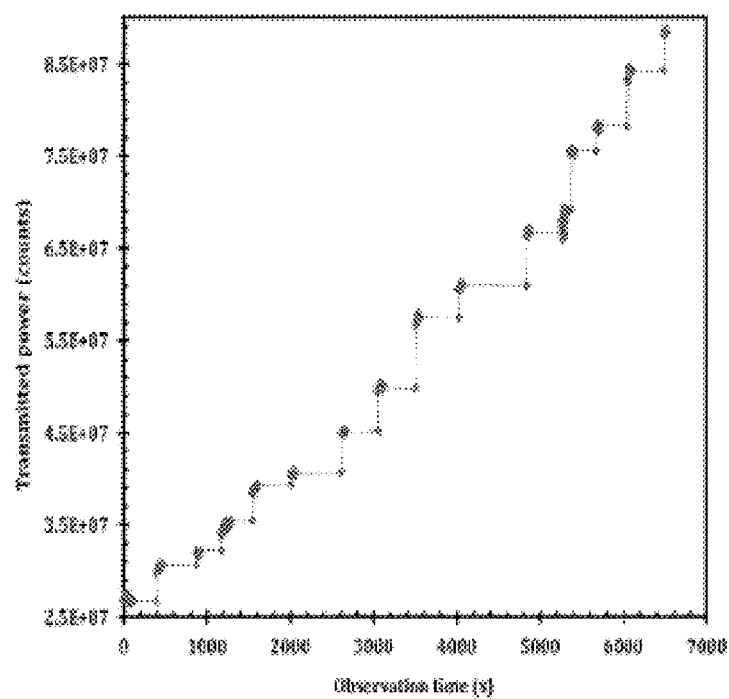
FIG. 16 is a plot of increasing transmitted power as a function of removed mass off a wafer by polishing.

In order to demonstrate the resolution of mass removal of a silicon wafer by polishing, a piece of Si-wafer was gradually polished by hand on an 800-grit sand paper. The wafer was weighed after each polish by a lab microbalance, mounted on the terahertz (THz) spectrometer and transmitted power (in counts) vs. the removed mass was recorded. FIG. 16 shows that as the mass is removed by polishing, the transmitted power increases successively for each polish, indicating that transmitted power is an inverse function of removed mass. The results were used for computing the corresponding thickness from known area and density of the wafer.

Figure 17:
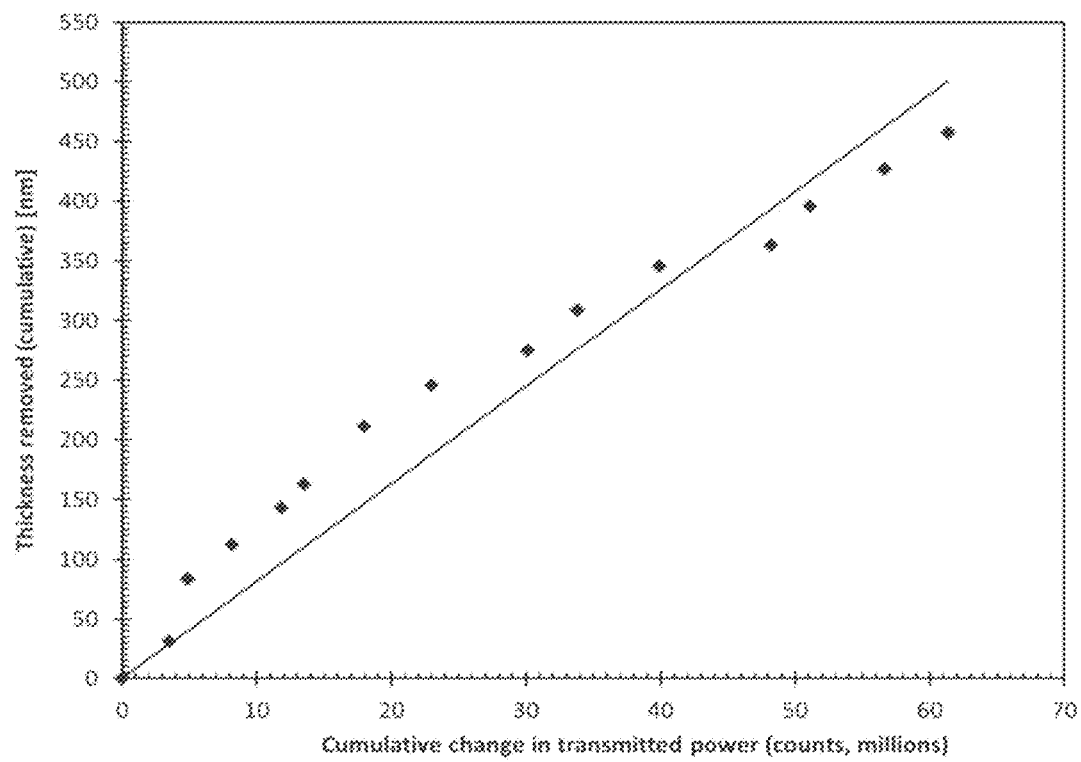
FIG. 17 is a plot of computed cumulative layer thickness removed vs THz transmitted power (counts)

FIG. 17 shows the computed thickness vs. the change in measured power. The slope of FIG. 17 indicates that for each nanometer thickness removed, the counts difference is 8.15 million. The noise floor of the detection system is ~±5×10$^3$ counts. Thus, the uncertainly in the thickness data of FIG. 8 is <±10 μm. Therefore, it is demonstrated that THz transmission measurement can be used for high precision thickness monitoring of wafer's planarization process. Thus, a control system operated by this monitoring system is expected to maintain high level of uniformity of the CMP process. However, the actual CMP process involves use of polishing slurry and other chemicals. Therefore, the performance of this system must be determined via calibration for an actual CMP system. In addition, different calibration will be necessary for different slurry and polishing protocol combinations.

Figure 18:
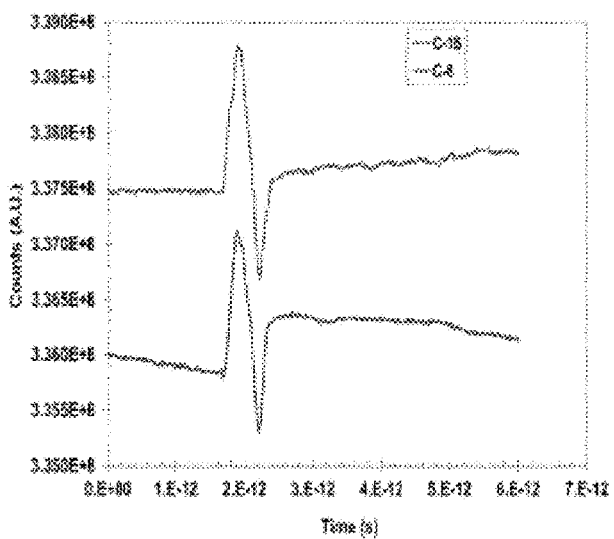
FIG. 18 is a temporal signal of silicon wafer coated with two different SAM.
Figure 19:
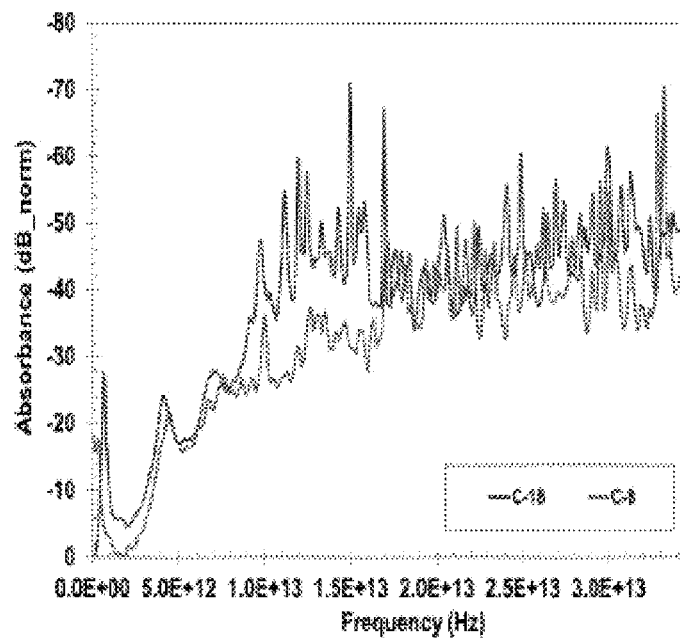
FIG. 19 is a plot of the absorbance spectra of two SAMs on silicon wafer.
Figure 20:
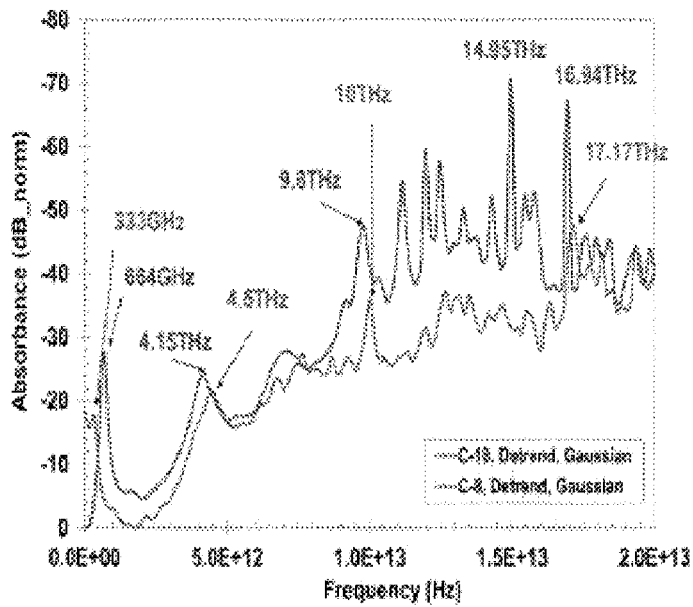
FIG. 20 is a plot of the absorbance spectra of both SAMs (same as FIG. 19 X-axis truncated to 20 THz)

Self-assembled monolayers (SAMs) were fabricated on double side polished silicon wafers. Two different SAMs have been used. (1): n-Octadecyltrichlorosilane (abbreviated as C-18), Mw=387.93 g/mol; and (2): 7-OCT-1-Enyltrichlorosilane (abbreviated as C-8); Mw=245.65 g/mol. As received SAM coated wafers were mounted on a THz spectrometer, Terahertz time-domain spectra were acquired with a TeraSpectra front end as manufactured by Applied Research and Photonics, Inc. FIG. 18 shows the comparison of time-domain signals of the two samples. The SAM C-8, having lower number of carbons, exhibit higher transmission compared to the SAM C-18. The Fourier transform absorbance spectra of both specimens are shown in FIG. 19. Here also the C-18 SAM-wafer exhibits higher absorbance than that of C-8 SAM-wafer; consistent with the higher Mw of C-18. FIG. 20 shows a close-up of FIG. 19 where several peaks are identified by their frequency that may be used as distinguishing features between the two SAMs. The absorbance of C-18 SAM is always higher than that of C-8 SAM; this observation is consistent with C-18's higher Mw. The spectra shows clear identifying characteristics between the two SAM species.

A terahertz scanner has been used to detect defects in a semiconductor wafer. A high resolution scan clearly shows the start, the end, and intricate patterns for each die on a wafer. Since the scan is in scale in all three dimensions, the defect position may be pin pointed. Terahertz reconstructed imaging allows visual inspection of wafers both on the surface and also the layers under the surface in a non-destructive fashion. All measurements are done by non-contact means. It is also demonstrated that terahertz transmission measurements may be used with high precision for monitoring and controlling wafer CMP process. The technique may be extended to other substrates transparent to terahertz radiation. Terahertz spectroscopy can be effectively used to identify different SAM coated silicon wafers for the SAM species. Two SAMs used here are 8 and 18 carbons long, respectively. The C-18 SAM-wafer exhibits higher absorbance than C-8. This is assigned to the higher molecular weight of C-18. The Fourier transform absorbance spectra of both specimens also exhibits higher absorbance for C-18 than that of C-8 SAM-wafer. This is also consistent with the higher Mw of C-18. Thus the terahertz system of the present study offers a reasonable and accurate solution for different aspects of wafer inspection, thereby aiding to reduce the wafer rejects during fabrication.

Figure 21:
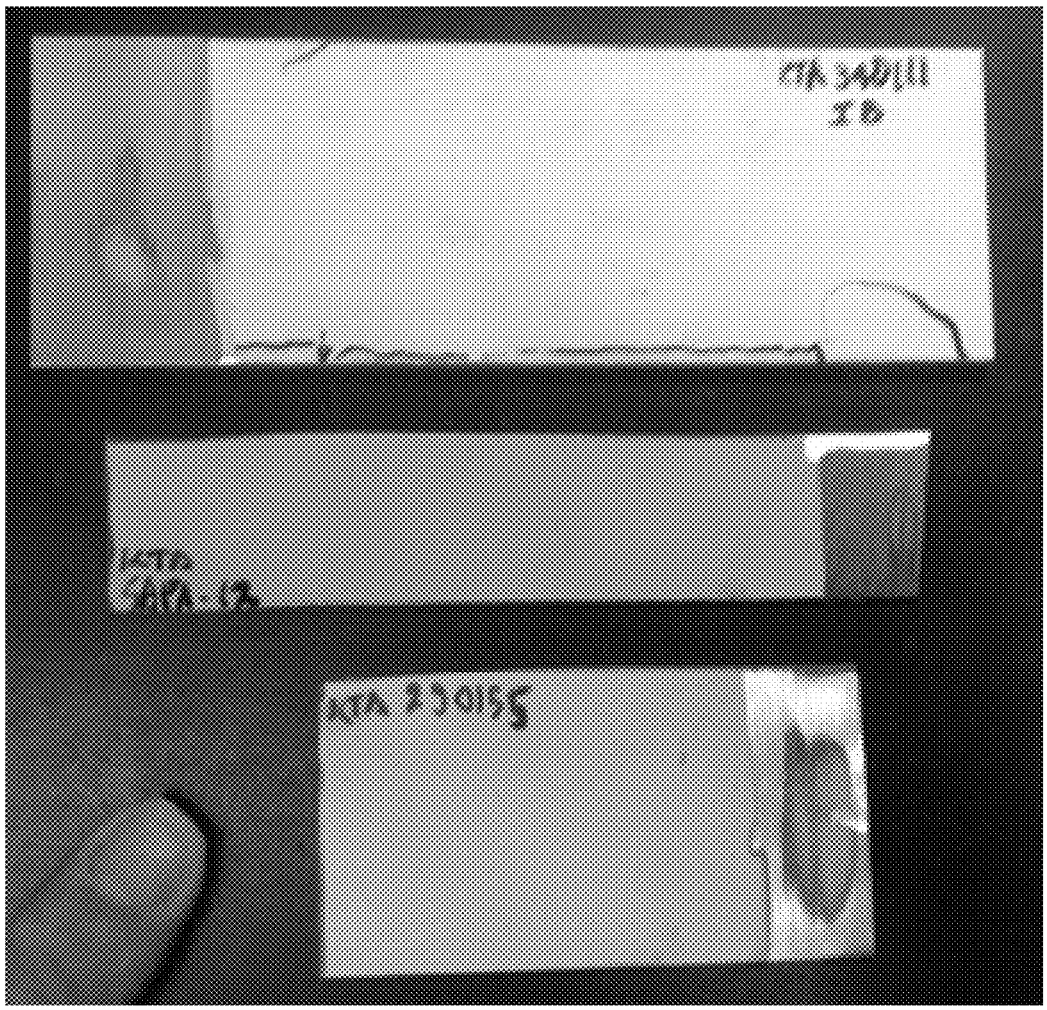
FIG. 21 shows three samples.

FIG. 21 shows three samples for testing: 1) KTA 340111 IB-a segment from an aluminum handrail with a powder coated topcoat, and may have a very thin primer/sealer; 2) KTA SAPA 12-a segment from an aluminum piece with a wash primer pre-treatment, a white primer and a white topcoat; and 3) KTA 290155-a segment from a steel metal roof-perhaps strip galvanized, with an unknown coating system.

Figure 22:
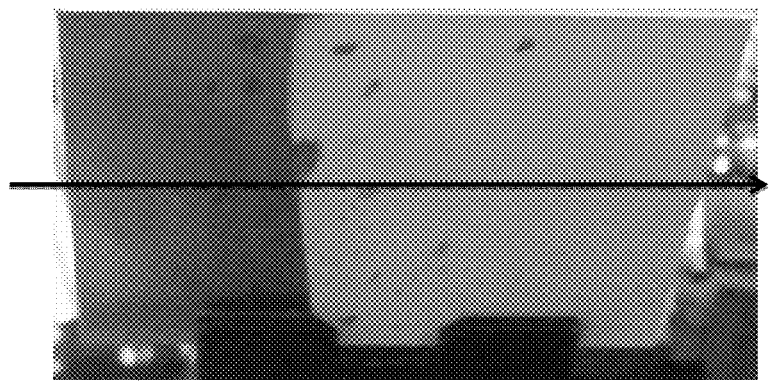
FIG. 22 shows a piece of sample mounted on the scanner.
Figure 23:
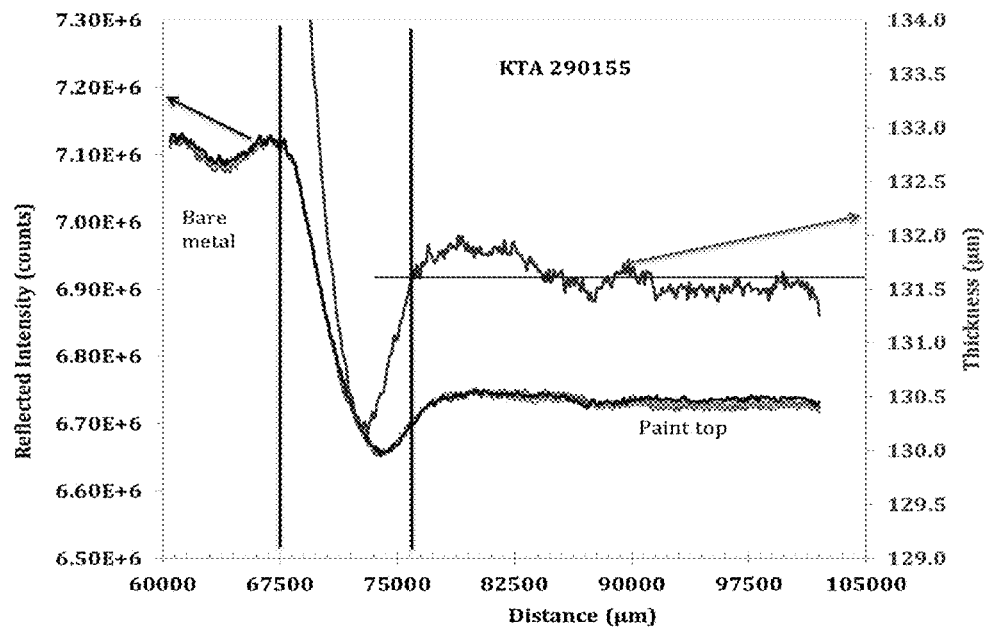
FIG. 23 shows traces of scan.

The coating on one end was removed by power sanding to bare metal that serves as the reference. FIG. 22 shows a piece of sample mounted on the scanner. Traces of the scan are shown in FIG. 23 (left Y-axis). It was scanned along the direction indicated by the arrow. Several trials were taken; all traces overlap showing good reproducibility. Bare metal exhibits higher reflection than painted surface. Thickness (right Y-axis) was modeled based on the measured traces. Average paint thickness for this sample is ~131.7 μm (±2 μm) as indicated in FIG. 23.

Figure 24:
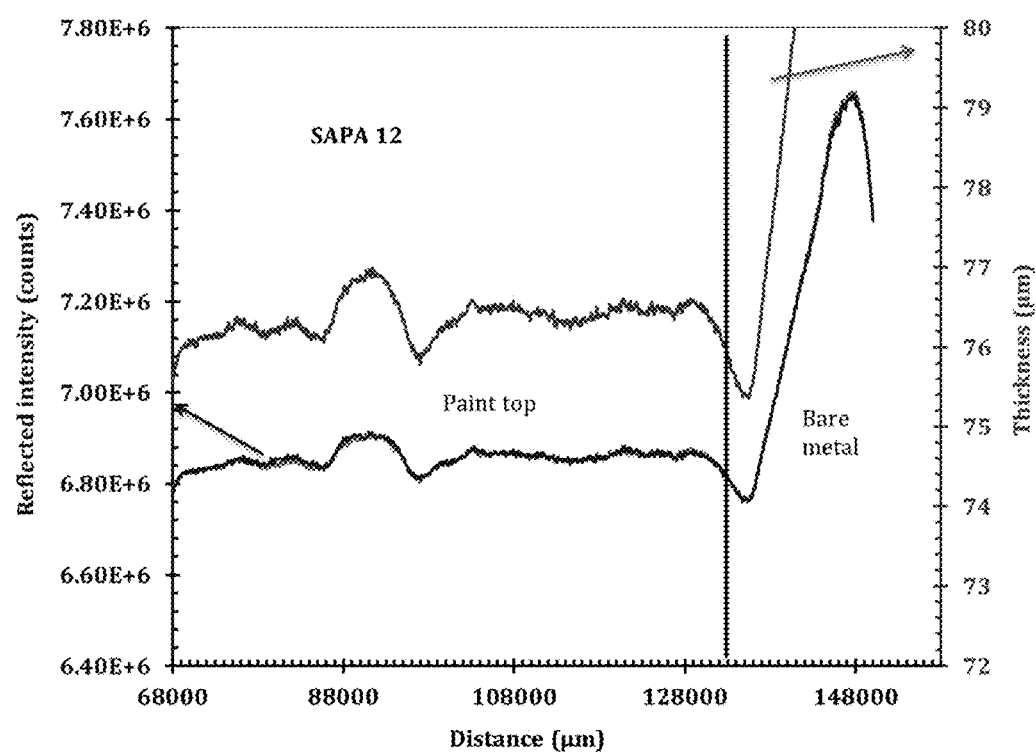
FIG. 24 shows scanned traces (left Y-axis) for sample SAPA 12.
Figure 25:
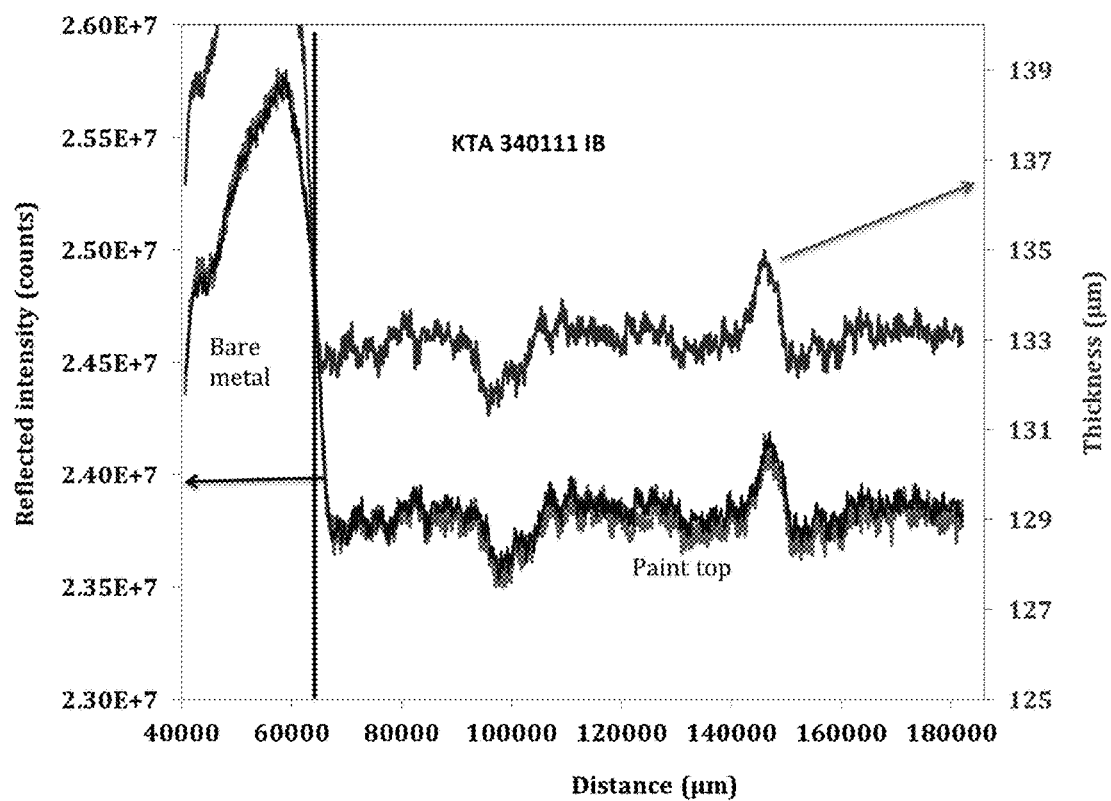
FIG. 25 shows scanning traces (left Y-axis) and thickness (right Y-axis) for sample KTA 3440111 IB.

Scanning data and thickness results for sample SAPA 12 are shown in FIG. 24 and the same for the sample 340111 IB are shown in FIG. 25. FIG. 24 shows scanned traces (left Y-axis) for sample SAPA 12. Average Paint thickness (right Y-axis) was determined to be ~(76.5±1) μm. FIG. 25 shows scanning traces (left Y-axis) and thickness (right Y-axis) for sample KTA 3440111 IB. Paint layers are determined by scanning across the depth (thickness) of the paint as described herein.

Figure 26:
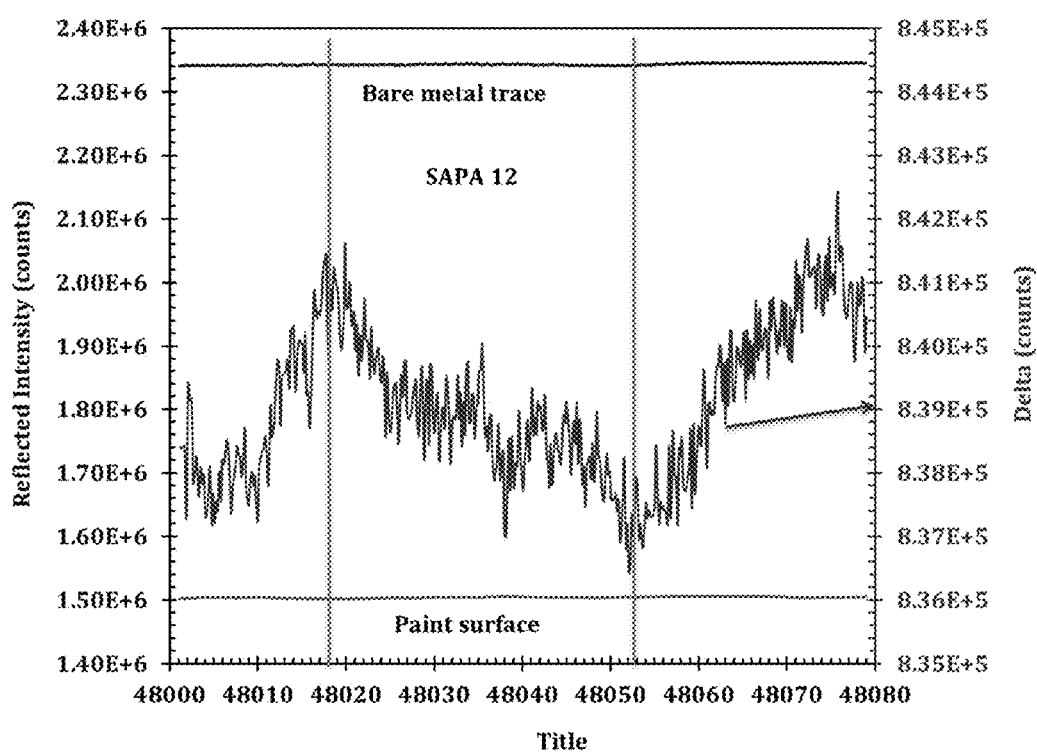
FIG. 26 shows the thickness profile (right Y-axis) of paint on top of the substrate for sample SAPA 12.

FIG. 26 shows the thickness profile (right Y-axis) of paint on top of the substrate for sample SAPA 12. The total thick is estimated to ~80 μm. The inflection in the profile at the vertical demarcation lines at ~18 μm and at ~53 μm are likely to be an indication of the interfaces between the layers of paint. Thus the layers are likely to be composed of a first layer of thickness ~18 μm, a second layer of thickness ~35 μm and a third layer of thickness ~27 μm.

Figure 27:
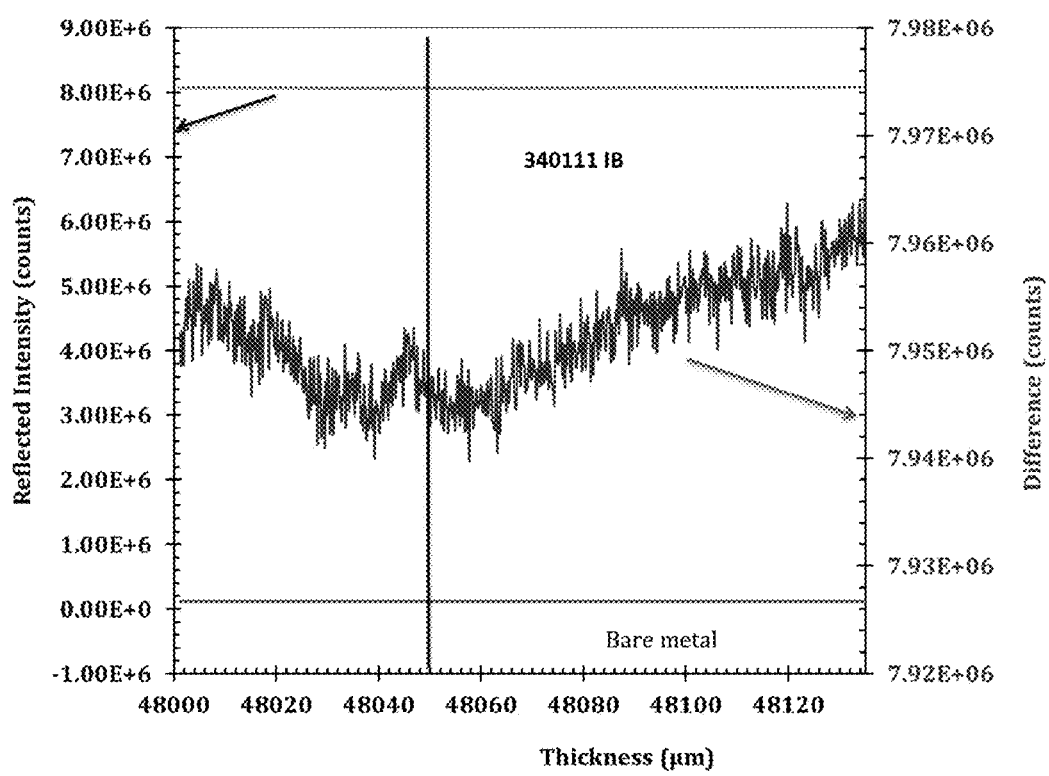
FIG. 27 shows a thickness profile (right Y-axis) of paint on top of the substrate for sample 340111 IB.

FIG. 27 shows a thickness profile (right Y-axis) of paint on top of the substrate for sample 340111 IB. The total thick is estimated to ~135 μm. The inflection in the profile at the vertical demarcation line (~50 μm thickness) is likely an indication of the interface between two layers of paint. Thus the layers are likely to be composed of a first layer of thickness ~50 μm and a second layer of thickness ~85 μm.

Figure 28:
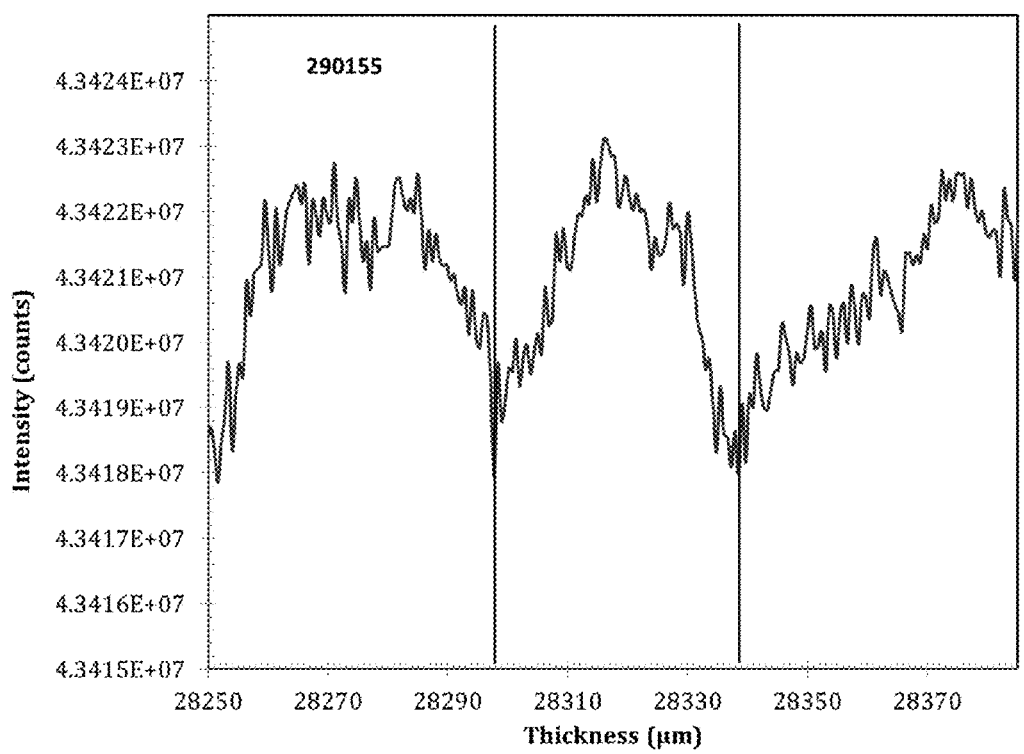
FIG. 28 shows a scan across the paint on sample 290155.

FIG. 28 shows a scan across the paint on sample 290155. Total thickness of the paint is estimated to be ~132 μm. The demarcation lines indicate the presence of 3 layers.

Described herein is a terahertz scanning reflectometer system is described herein for spectral profiling and imaging of surface and sub-surface of biological tissues (e.g., skin) in a non-invasive fashion. In particular, a high sensitivity terahertz scanning reflectometer (TSR) is used to detect early signs of cancer via terahertz spectral profiling and imaging.

Terahertz scanning reflectometry offers an opportunity to investigate both the surface and the sub-surface of biological tissues (e.g., skin) in a non-invasive fashion. The non-ionizing nature of T-ray eliminates radiation damage or perturbation of sensitive tissues while still able to probe disease conditions in the deeper layers leading to an effective early diagnostic tool. For example, thickness profiling of benign and cancerous skins would show vast difference in their profile. A terahertz technique has been developed that is comprised of terahertz scanning reflectometry, terahertz time-domain spectroscopy and terahertz imaging for detection of cancerous skin with basal cell carcinoma (BCC), melanoma, and other malignancies in comparison to benign skin sample. Two groups of samples were studied: the first group of samples is benign skin biopsy and the second group of samples is biopsy from cancerous area. Thickness profiling exhibits significant differences in profiles of the respective skin samples both in their layer structure and also in their total reflected intensities; thus indicating presence and lack of cellular order for the respective specimens.

Similarly, terahertz spectra acquired in transmission exhibit quantifiable differences for both groups. Terahertz image of the benign skin shows regular cell patterns while the image of a sample with BCC exhibit no clear cell pattern. The lack of clear cell order in the skin, thus, may be used as an indication of cancerous area and this finding may be used as an early diagnosis tool. It is notable that this is the first of such a concerted observation of benign versus BCC skins from three different experiments. The results are consistent from individual experiments and collectively provide an accurate means of early detection of BCC, melanoma, and the like.

Described herein is a system and method for skin cancer detection and thickness profile determination.

Figure 29:
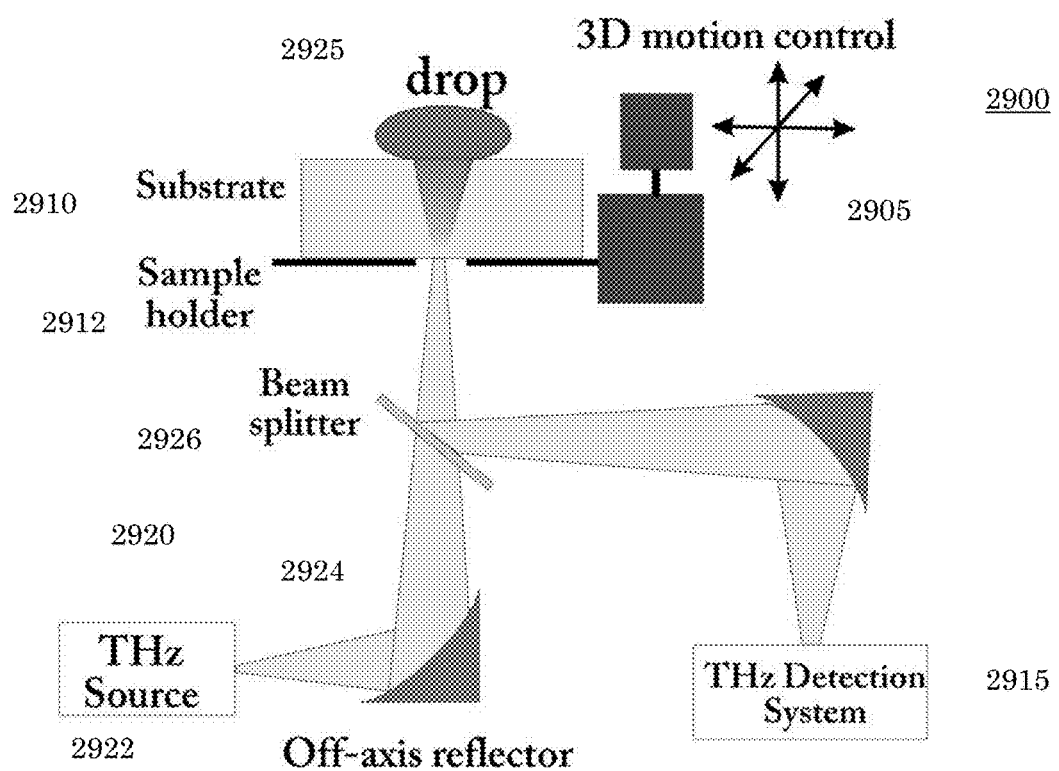
FIG. 29 shows an example terahertz scanning reflectometer.

FIG. 29 shows an embodiment of a terahertz scanning reflectometer 2900. The terahertz scanning reflectometer 2900 includes a fine pitch motion control system 2905 that is used to move a substrate 2910 positioned on a sample holder 2912 in and out of the focal point of a terahertz generator 2920 while a detection system 2915 may acquire data in real-time. For kinetics, a specimen 2925 is kept fixed and focused. The terahertz generator 2920 further includes a continuous wave terahertz source 2922 configured to generate terahertz radiation, an off-axis parabolic reflector 2924 configured to focus the terahertz radiation at a surface of the substrate 2910 and a beam splitter 2926 configured to direct a reflected beam from the sample holder to the detection system 2915.

FIG. 29 illustrates a continuous wave terahertz scanning reflectometer (CWTSR) measurement system. The CW terahertz source 2922 is used to generate the terahertz radiation from an electro-optic dendrimer via dendrimer dipole excitation (DDE). As shown in FIG. 29, the terahertz beam is focused on the specimen 2925 at 90° angle via an off-axis parabolic reflector 2924 (normal incidence). The beam reflected by the substrate 2910 is directed to the detection system 2915 via the beam splitter/combiner 2926. The specimen cell is comprised of a scanning platform 2912 that is controlled by the high precision motion control system 2905. This arrangement allows direct measurements as follows. The off-axis parabolic reflector 2924 is adjusted such that initially the terahertz beam remains focused on the substrate surface 2910. At this position, the Z-axis of the motion control can be engaged for scanning the substrate 2910 to interrogate the reflectance across its thickness. Under the assumption that the reflectance is proportional to the physical properties of the incident layer, (e.g., the density), a vertical scan will produce the thickness profile of the substrate, as explained below.

The motion controller 2905 can be engaged to move the focal point inside the substrate 2910 to interrogate the reflectance at the point of incidence and then gradually across the thickness; this gives the ∂C/∂x at the point of incidence when the reflectance of the blank substrate (reference) is subtracted from the reflectance of the specimen, $$\left| \frac{\partial C}{\partial x} \right|_{Specimen} = \left| \left| \frac{\partial C}{\partial x} \right|_{SampleScan} - \left| \frac{\partial C}{\partial x} \right|_{Reference} \right| \quad (2)$$

The measured reflectance, thus, may be utilized to deduce the layer-structure of the specimen by point-by-point scanning of the whole thickness.

Further, the Z-axis may be locked on a given layer and an area scan may be conducted to generate a surface plot of that layer. When a XYZ scan is conducted, a 3D reconstructed image may be generated by sequential layer by layer scans.

Described herein is terahertz time-domain spectroscopy.

When THz radiation interacts with molecules, it will stimulate many resonances such as molecular vibrations, and/or other resonances due to translation, rotation, torsion, and even conformational changes. Therefore, terahertz interaction will result in the incident photons being affected by characteristic quantities determined by a specific interaction or by multiple interactions. The change in energy and/or frequency yields information about the molecular nature of the interaction. Molecular simulation, especially molecular dynamics, reveals that there are numerous resonances and conformational states possible when a molecule is not at its lowest energy state. As most material remains at its lowest energy state under normal and steady state conditions, THz perturbation will stimulate possible available states in the low frequency regions. Therefore, the transmitted beam will carry information about the material; and equivalently the reflected beam will also carry information about the nature of the matrix. Quantitative prediction of such information is obviously materials specific and best determined by experimental measurements. Notably, biological systems are almost never at equilibrium. Hence, terahertz interactions may also be exploited to study the dynamic nature of a biological system.

Described herein is reconstructive imaging.

The intensity of the reflected terahertz beam is proportional to the specific features of the specimen under test. Therefore, measured intensity may be modeled in terms of suitable physical parameters such as refractive index, density, dielectric constant, etc., via a modified Beer-Lambert's law. If all material parameters are assumed to remain unchanged during measurements, because, terahertz radiation is non-ionizing and does not perturb the intrinsic properties, then the reflectance, R, will be proportional to the variations in material properties at the point where the beam is incident. For human skin, although a wide variation of physical properties such as density is not expected, however, water and fat contents of different layers of skin will vary significantly. As such, the reflectance is dependent on the spatial and angular coordinates: R(x, y, z, θ). Therefore, a 3D reconstructed image generated from reflectance, or equivalently, from transmittance, will yield the characteristic cellular patterns of the skin.

Another advantage of the terahertz scanner is that scanning is conducted across the thickness of skin for interrogation of internal layers. This is only possible with terahertz radiation because the energy is capable of penetrating inside the skin without any harmful effect since the energy is non-ionizing. Based on the above principle, a signature of a given feature may be established. Moreover, feature size may be estimated from either a 2-D scanned profile and/or a 3-D scanned reconstructed image. The terahertz nanoscanner deploys a non-contact measurement system with an adjustable stand-off distance. The sample space is adjustable to accommodate required sample size. A rotary axis enables examination of a sample from different viewing angles. This is important because some features and non-uniformities might not be along a straight line-of-sight. Thus an angular scan enables viewing hidden features. In addition, with the advent of the angular axis, one can scan cylindrical objects in a conformal fashion.

Figure 30:
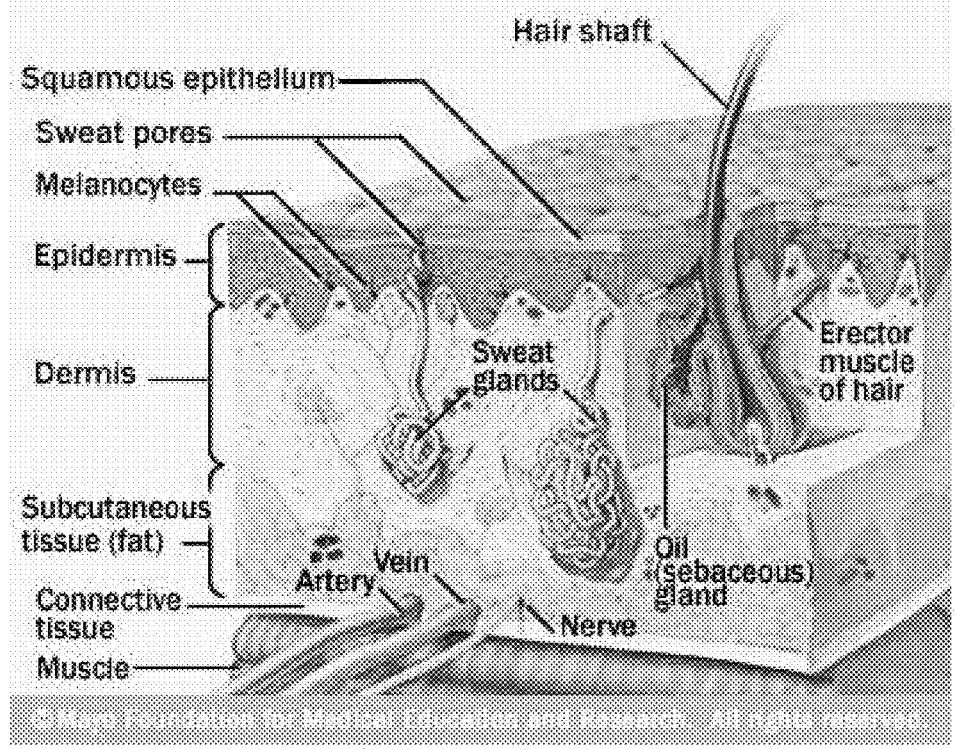
FIG. 30 shows an example of human skin with different constituents and layers.

FIG. 30 shows a cartoon of different anatomical features of human skin cross section. A vertical scan (thickness profile) is thus expected to exhibit layering information. However, it can also be assumed from FIG. 30 that the layering pattern will be different at different spots on the skin because the thickness profile is not the same at every place. Nonetheless, it is expected that a layered pattern of some kind will be present for the benign skin while the cancerous skin will exhibit diminished layered structure due to cell agglomeration and loss of regular cellular pattern.

The excised skin tissue samples were collected from consenting patients undergoing Mohs' Micrographic Surgery. These skin samples were stored in dry ice until a few minutes before the measurements. Thickness profiles, terahertz spectra, and reconstructed images were taken within two days of collecting the samples. Samples were taken from four different patients. Some of these samples were benign, noncancerous and some were cancerous.

All samples were mounted on a high density polyethylene (HDPE) plate. Measurements were done one at a time, thus the same background was valid for all measurements. For example, a benign sample (14-50a) was attached on the HDPE holder and loaded into the CWTSR, and a thickness profile was recorded. This sample was then loaded into the terahertz time-domain spectrometer, TeraSpectra. Terahertz spectrum was recoded with the spectrometer's front-end software. Thickness profiles and terahertz spectra were taken in the same manner for each remaining samples. Additionally, a few samples were mounded on a nanoscanner for ZYX scanning for reconstructive imaging. Thickness profiles, terahertz spectra, and reconstructed images were analyzed to study the characteristic features of the benign and cancerous skin tissues and to assess any significant differences between them.

Figure 31:
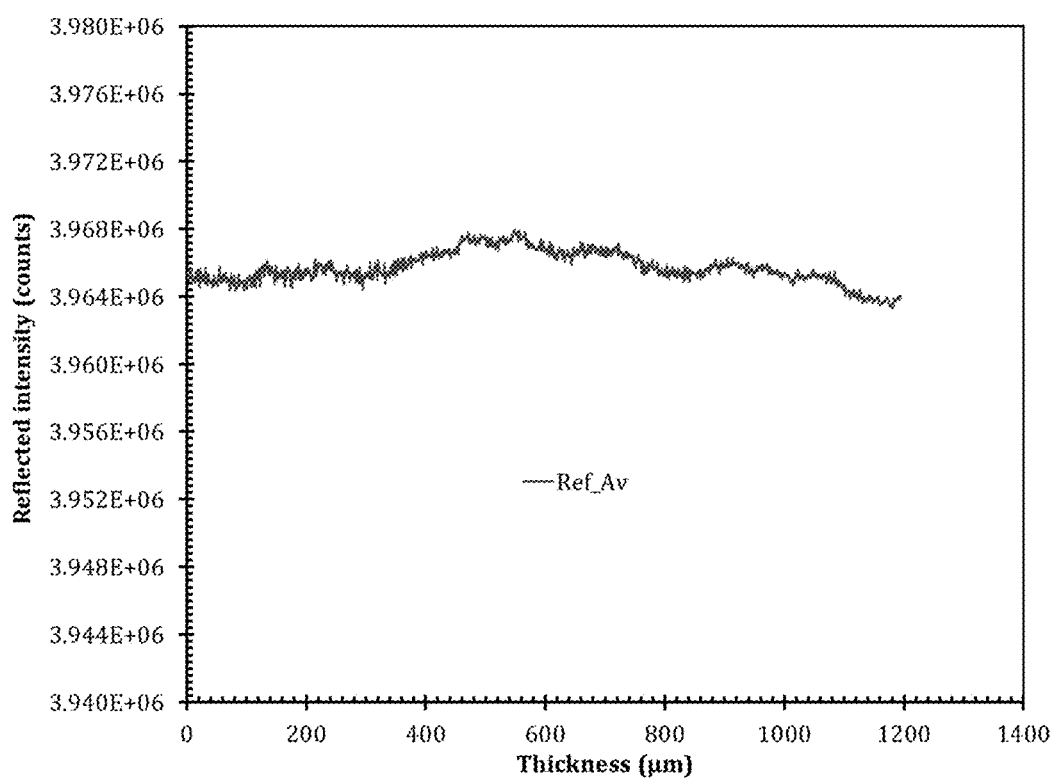
FIG. 31 shows a thickness profile of an empty cell used as a reference.

FIG. 31 exhibits thickness profile of the empty cell. This is used as the reference for all subsequent measurements. Several trials were taken at an interval of ~5 minutes that were averaged to obtain the average reference; Ref_Av. Average error limit was calculated to be 2295 counts.

Figure 32:
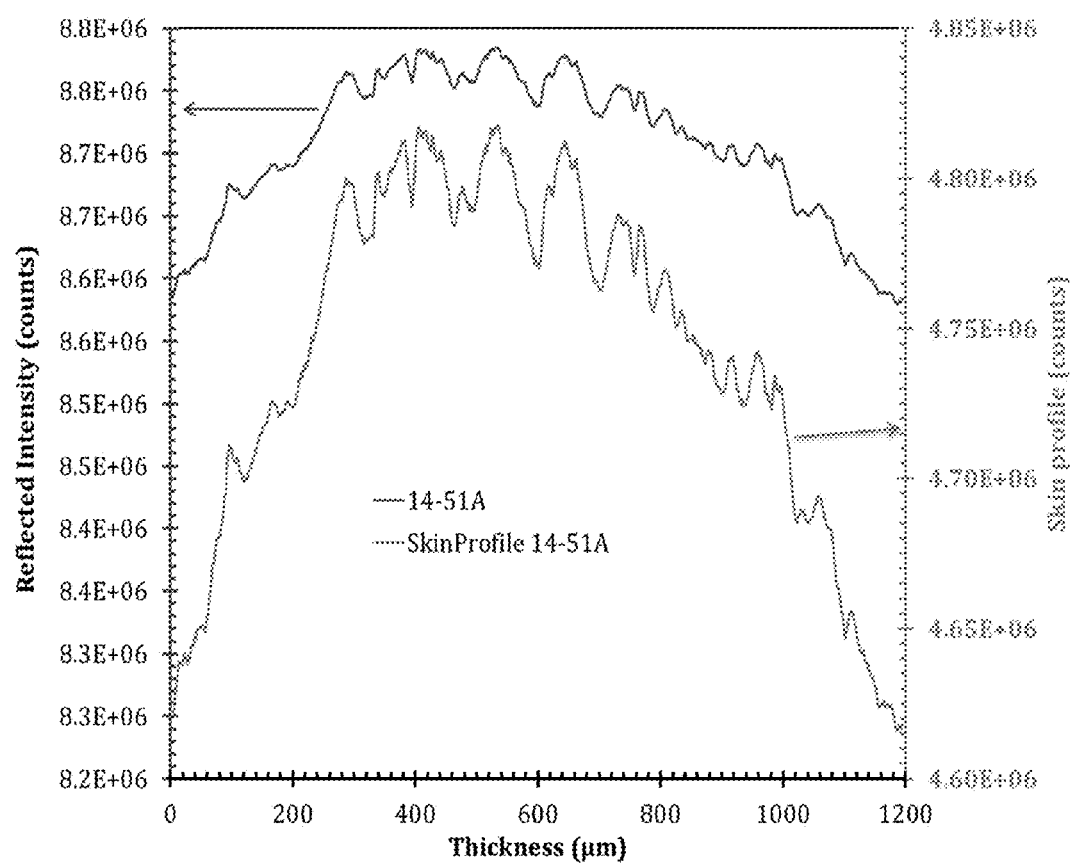
FIG. 32 shows a thickness profile from scan of a benign skin sample.

FIG. 32 shows the thickness profile scan of a benign sample (#14-51A, left Y-axis). The skin thickness profile (right Y-axis) is obtained by subtracting the reference (FIG. 3) from the scan of the skin sample. As seen from FIG. 32 (right Y-axis), the reflected intensity exhibits increasing trend as the beam focal point is penetrated through the skin thickness. The fluctuations in the intensity are indicative of the layered structure of the skin. As the beam penetrates deeper, more photons are absorbed be the skin cells of different layers, thus decreasing the reflected intensity. A clear layering pattern is also visible from this plot.

Figure 33:
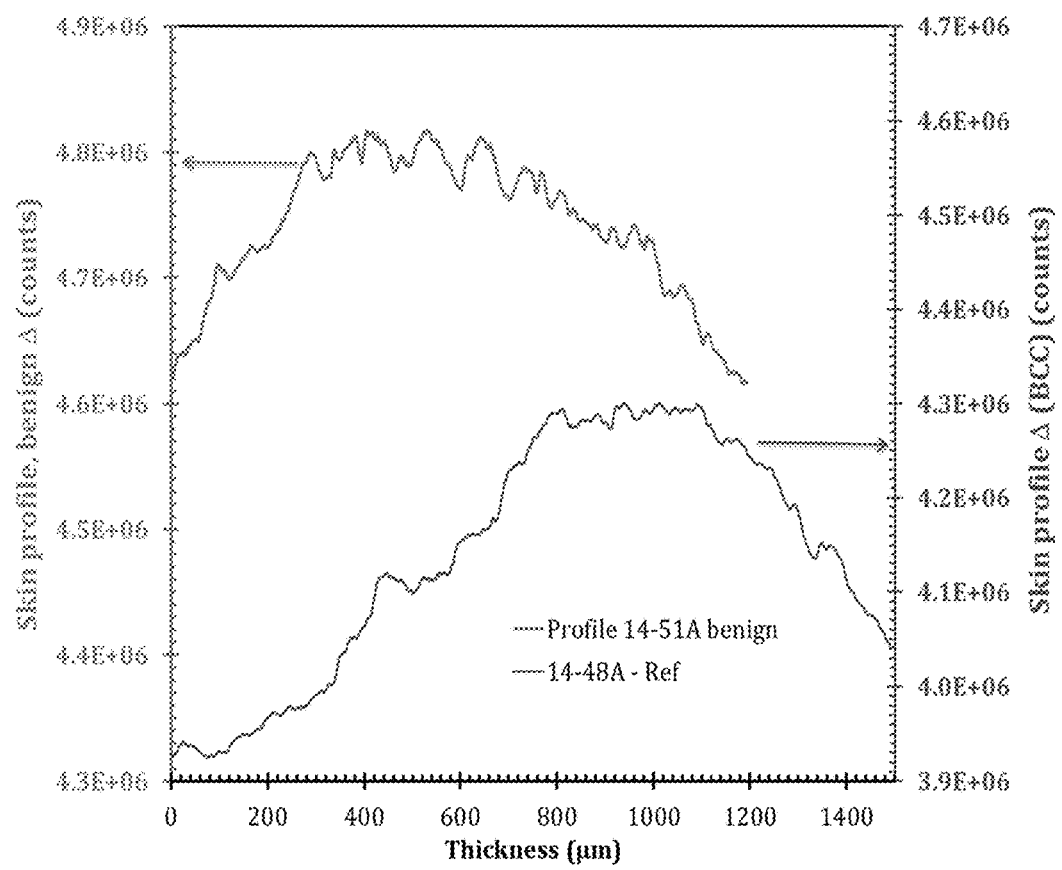
FIG. 33 shows a thickness profile of benign skin (left Y-axis) and skin with basal cell carcinoma (right Y-axis)

FIG. 33 shows the thickness profiles of benign skin (left Y-axis) and a sample with basal cell carcinoma (right Y-axis). These profiles exhibit significant differences between the benign and cancerous skin profiles both in their layer structure and also in their total reflected intensities. The presence of layers is visible for the benign skin while the layer definition of BCC sample is clearly distorted. Also, the cancerous skin exhibits lower reflected intensity (right Y-axis of FIG. 33) compared to benign skin sample (FIG. 33, left Y-axis). This is indicative of a higher reflectivity of benign skin due its regular cellular order while the lack of regular cell pattern of the BCC is either absorbing more radiation or being relatively more transparent or both.

Figure 34A:
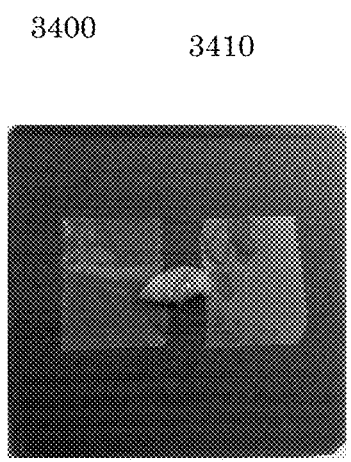
FIGS. 34A and 34B show a biopsy skin sample fixed on a high density polyethylene plate (left) used as a sample cell that has an opening for terahertz transmission only through the specimen and the cell is then mounted on a spectrometer (right)
Figure 34B:
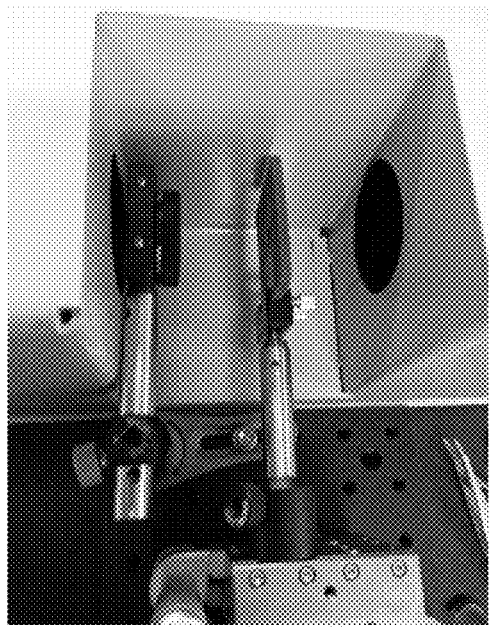

Terahertz time domain spectroscopy was conducted on both groups of samples. FIGS. 34A and 34B show a biopsy skin sample fixed on a high density polyethylene plate (34A) used as the sample cell that has an opening for terahertz transmission only through the specimen. The cell is then mounted on the spectrometer (34B) and the specimen is placed in the beam path with the help of a XYZ positioning stage. An iris is used to limit the beam such that the central part of the specimen is exposed.

FIG. 34A shows a skin sample (specimen) 3400 mounted on a HDPE plate 3410. The HDPE plate 3410 used as the sample cell has an opening for terahertz transmission through the specimen without being barred by the cell. The cell is then mounted on the spectrometer 3415 and the specimen 3400 is placed in the beam path with the help of a XYZ positioning stage 3420 (FIG. 34B). An iris is used to limit the beam such that the central part of the specimen is exposed. This ensures all specimens are exposed in the same way with identical intensity. The time-domain signal is acquired by the front-end software of the spectrometer.

FIGS. 35A and 35B show the time-domain signal (interferogram) of benign skin sample (35B) and BCC biopsy sample (35A). Both samples were mounted on the same holder, one at a time and spectra were acquired successively. Thus it was ensured that both samples have identical background. As seen from FIGS. 35A and 35B, the time-domain signal of the sample with BCC is significantly different than that of the benign skin sample. It is noted that the transmitted intensity of the BCC skin sample is higher than that of the benign skin sample. This is consistent with the findings from thickness profile (FIG. 33) where the BCC skin sample has a lower reflectance than the benign skin sample. Fourier transform is conducted as a standard practice for extracting frequency domain spectra from the time-domain signal (interferogram).

However, because of very high sensitivity of terahertz interaction with materials, usually the Fourier transform will result in to a multitude of peaks in the frequency spectrum as described herein below. Often there is no ready explanation of these additional peaks in the absorbance spectrum, for example, for nonstandard soft material such as human skin. Hence it is advantageous to reduce the number of peaks to a few characteristics ones. Therefore, here we utilize a different procedure, the Eigen Frequency Analysis. Eigenvalues and eigenvectors are properties of a mathematical matrix; when the matrix is composed of material parameters, then one can extract particular property of interest. Eigen analysis frequency estimation algorithms offer high-resolution frequency estimation. These procedures are perhaps the most accurate procedures for estimating harmonic frequencies.

Figure 36:
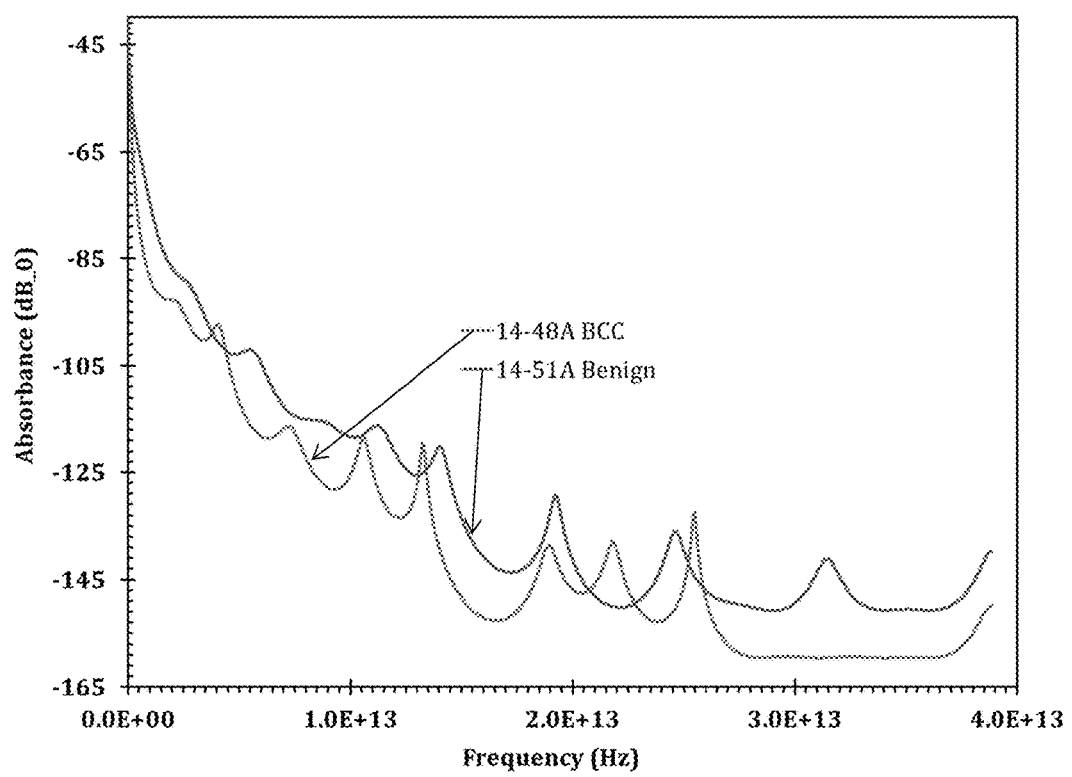
FIG. 36 shows Eigen frequency absorbance spectra of benign and cancerous skin samples.

FIG. 36 exhibits the Eigen frequency absorbance spectra corresponding to the time-domain signal or interferogram shown in FIGS. 35A and 35B. Here the benign and BCC skin samples yield their respective spectral signatures.

Figure 37A:
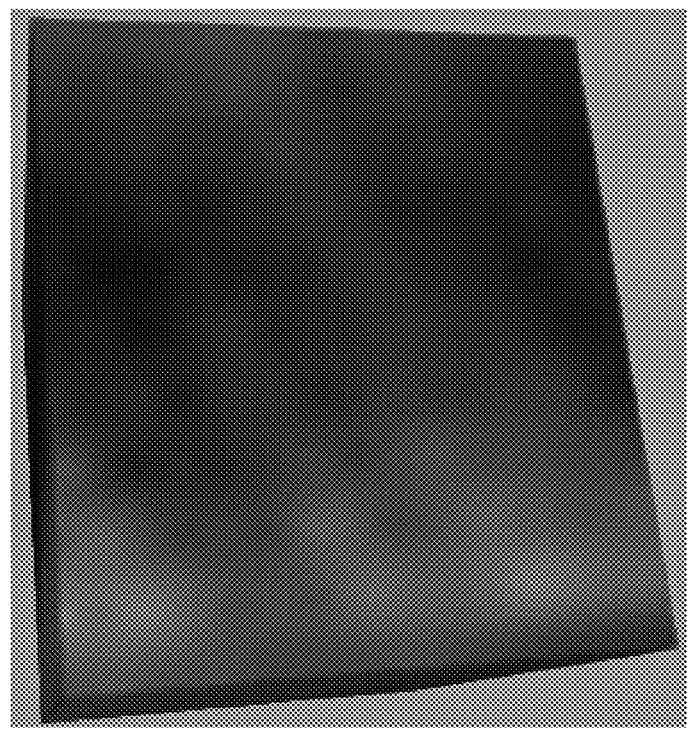
FIGS. 37A and 37B show econstructed 3D image of healthy skin (37A) and skin with basal cell carcinoma (37B). Reconstructed 3D image of healthy skin (left) and skin with basal cell carcinoma.
Figure 37B:
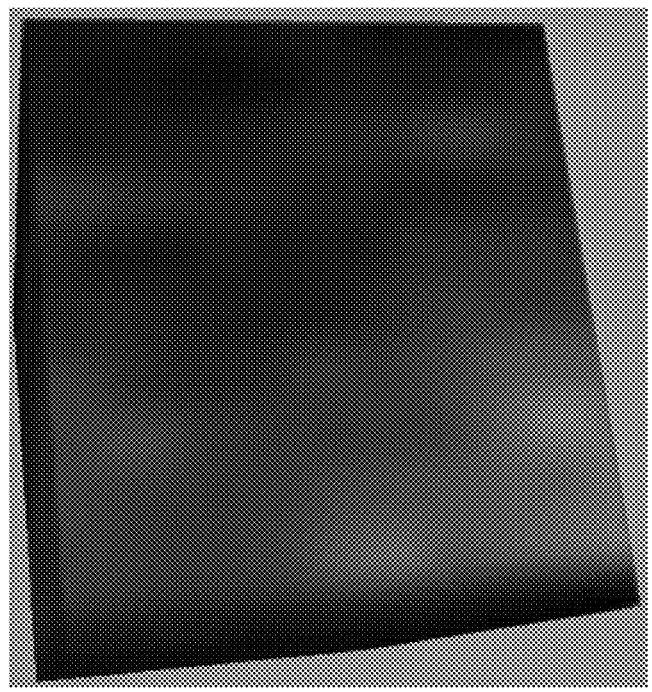

FIGS. 37A and 37B show the reconstructed 3D image of healthy skin (37B) and skin with basal cell carcinoma (37A). Healthy sample was scanned over 1 mm×1 mm×1.2 mm and the BCC sample was scanned over 1 mm×1 mm×1.5 mm, because, the cancerous skin is expected to be thicker than the benign skin. The top surface of healthy skin shows regular cell pattern (37B) while the BCC sample exhibits a lack of regular cell patterns. Therefore, the lack of normal cellular pattern is indicative of cell agglomeration due to BCC. This feature, thus, may be used as a metric for early detection of the BCC.

Terahertz technology has been deployed for detection of skin cancer and in particular, basal cell carcinoma. Three different terahertz techniques have been exploited including scanning reflectometry for thickness profiling, time-domain spectrometry for spectral analysis and high resolution 3D reconstructed imaging for visual inspection of cancerous versus benign skin samples.

FIG. 38 shows a sample of the data collected for 3D imaging. These data is processed by a software engine for converting to a reconstructed image of the region from where the data were collected. First the data are converted to grids; the grids are then painted to generate the image. Several different gridding algorithms may be deployed. Each method can result in a different representation of the data. Common gridding methods include: Inverse Distance to a Power; Local Polynomial and Data Metric.

Described herein are different gridding methods. First, the Inverse Distance to a Power Gridding Method is described. The Inverse distance method is a weighted average interpolator. This can be either an exact or a smoothing interpolation. Here, data are weighted during interpolation such that the influence of a point declines with distance from the lattice node. Weighting is assigned to data using a weighting Power that controls how the weighting factors drop off as the distance from a lattice node increases. The greater the power, the less the "effective points" far from the lattice node have during interpolation. As the power increases, the lattice node value approaches the value of the nearest point. For a smaller power, the weights are more evenly distributed among the neighboring data points.

Inverse distance normally behaves as an exact interpolator. When a grid node is calculated, the weights assigned to the data points are fractions, and the sum of all the weights is equal to 1.0. When a particular observation coincides with a lattice node, the distance between that observation and the node is 0.0, and that observation is given a weight of 1.0 while all other observations are given weights of 0.0. Thus, the grid node is assigned the value of the coincidental observation. A Smooth parameter may be used that serve as a mechanism for buffering this behavior.

Described herein is the Local Polynomial Gridding Method. The Local polynomial method assigns values to lattice nodes by using a weighted least squares fit with data within the search ellipsoid. For each lattice node, the neighboring data are identified by the user-specified Search type and Count. Using only data that match the search criteria, a local polynomial is fit using weighted least squares; the lattice node value is set equal to this value.

Described herein is the Data Metric Gridding Method. The Data Metric method is used to calculate statistical values using the data points found within the search. Define the search with the Search Type parameters. These search parameters are applied to each grid node to determine the local data set.

In addition, the system may be fitted with a fiber-optic probe for diagnosing skin cancer and other malignancies on live patients. Testing on live patients may be conducted to avoid unnecessary biopsies for the determination of a disease condition.

Described herein is a dendrimer based Terahertz time-domain spectroscopy and applications in molecular characterization. Difference frequency generation (DFG) (or two-photon excitation) not only eliminates the use of an expensive femto-laser, it also allows for producing both continuous wave (CW) and pulsed terahertz radiation, as well as higher output power and tunable terahertz range. A chromophore doped and poled poly(amido amine) dendrimer can produce ~3.4 mW terahertz power when pumped by two fiber coupled diode lasers with a combined pump power of ~5.5 W. Thus the terahertz figure of merit of this source is $1.124 \times 10^{-4}$ $W^{-1}$. This was achieved by means of the higher electro-optic coefficient of the EO Dendrimer.

Figure 39:
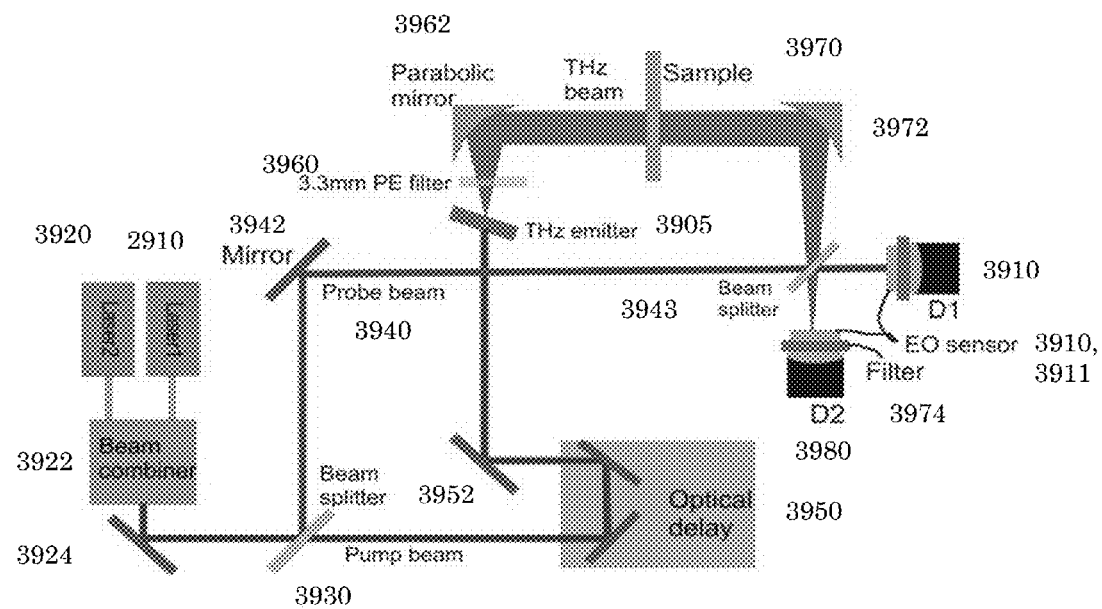
FIG. 39 shows an embodiment of a terahertz scanning reflectometer.

FIG. 39 illustrates the functional diagram of a terahertz time-domain spectrometer (THz-TDS) 3900 where the EO Dendrimer is used as the terahertz emitter 3605 as well as sensors 3910 an 3911. Two diode lasers (3915 and 3920) at 1064 nm and 945 nm are used, respectively; consequently, a range of ~35 THz is expected. A compact layout is achieved by arranging the components in the manner shown in FIG. 39. The diode lasers 3915 and 3920 are coupled to a beam combiner 3922, which in turn feeds the combined beam through a mirror 3924 to a beam splitter 3930. A probe beam 3940 is directed via a mirror 3942 and through a beam splitter 3943 and a sensor 3910 to a detector 3945. A pump beam 3943 is directed to the THz emitter 3905 via an optical delay 3950 and mirror 3952. The THz emitter 3905 emits terahertz radiation through a PE filter 3960, off of a parabolic mirror 3962 and through a sample 3970. The beam coming out of the sample 3970 is directed to detector 3980 via a parabolic mirror 3972, through beam splitter 3943, sensor 3911 and filter 3974.

An interferogram is generated when the stationary beam is scanned by the terahertz beam whose intensity distribution is captured by the detector pair. A self-calibrating algorithm is implemented such that the effect of atmospheric moisture is minimized. That is, a sample must be placed in the spectrometer for it to be measured; otherwise, the spectrometer will reproduce the same (empty) characteristic spectrum. A slightly different algorithm called Fourier transform of unevenly sampled data (aka Lomb periodogram) was deployed to analyze the experimental data. This algorithm essentially defines a transform by suppressing spectral leakage. In practical measurements this "empty" spectrum will serve as the background but when the sample is placed on a substrate (e.g., glass slide), then the blank substrate spectrum will serve as the background.

Figure 40:
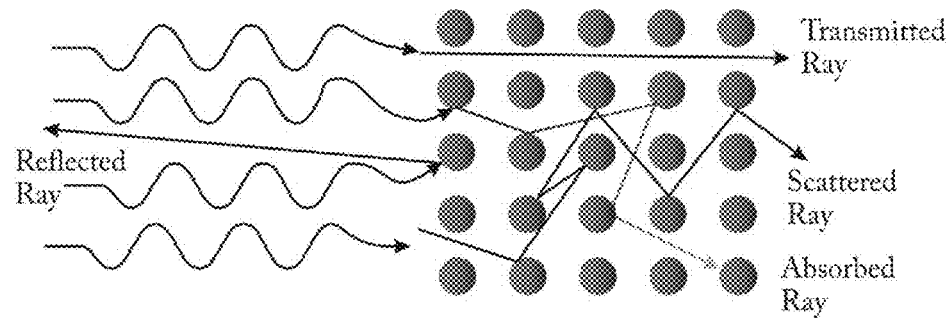
FIG. 40 shows an Interaction of photons with matter.

When THz radiation interacts with molecules, it may stimulate many resonances such as molecular vibrations, phonons and/or other resonances in the system (in general molecular "events"), resulting in the THz photons being affected by characteristic amounts determined by a specific interaction or event (see FIG. 40). The change in energy and/or frequency yields information about the molecular nature of the interaction. Infrared and Raman spectroscopy yields similar information but not capable of detecting many resonant states as can be detected with THz because terahertz photons are sensitive to the vibrational states of the entire molecule as opposed to just a bond or charge state. Molecular simulation, especially molecular dynamics, reveals that there are numerous vibrational and conformational states possible when a molecule is not at its lowest energy state. As most material remains at its lowest energy state under normal and steady state conditions, THz perturbation will stimulate possible available states in the low frequency regions.

FIG. 40 illustrates the interactions of radiation with a material system. The balls represent the lattice which may be composed of atoms for crystalline materials or of molecules (macromolecules) for amorphous and organic materials. Considering the lattice is composed of macromolecules, the material is most likely to be an amorphous matrix. In this case the transmitted beam will be composed mainly of the photons that have been involved in interaction with the matrix but not absorbed. Therefore, the transmitted beam will carry information about the material; and equivalently the reflected beam will also carry information about the nature of the matrix. Quantitative prediction of such information is obviously materials specific and best determined by experimental measurements.

Since terahertz interaction with molecules is sensitive to the vibrational modes of the entire macromolecule, THz-TDS has been successfully applied to characterize a number of molecular phenomena such as non-ionic detergents in biopharmaceuticals, transdermal drug delivery, single nucleotide polymorphism, DNA hybridization, and molecular chirality.

Because of its specific molecular selectivity, THz-TDS is promising for explosive detection. Many packaging or concealment materials are semi-transparent at THz frequencies. Because terahertz can penetrate in to many non-metallic containers, it is capable of identifying the explosive molecules within such containers. Because trace amount of explosives are present on these containers, a high sensitivity spectrometer may also be able to pick up explosive's signature from external traces as well. Wider terahertz bandwidth is expected to identify significant features in the acquired spectra specific to each molecule.

A key factor in remote identification of the explosives is the molecular signature recognition of the compounds from trace amount of residues. To achieve higher success rate and low false alarm, the technology must have very high sensitivity to pick up the right signature from very small amount of material remaining in the residue. Such sensitivity may be exploited to incorporate selectivity of the explosive materials by generating their terahertz spectral signature and building a library. Such libraries will also be useful for other initiatives. Another task will involve the design and implementation of an appropriate protocol for testing and deploying the devices in the field. Since terahertz is capable of penetrating through fog and sand storm, this technology is an ideal candidate for remote identification of explosives.

Another key factor for extended range (distance) detection is the intensity of terahertz radiation. While EO Dendrimer technology allows generation of milliwatts of terahertz power, this may be further enhanced via a chip based terahertz generator. This involves fabrication of terahertz chip from EO dendrimer that will enable terahertz amplification via waveguide technology [16].

The most commonly used military explosives are pentaerythritol tetranitrate (PETN), a nitrate ester; cyclotrimethylenetrinitramine (RDX), a nitramine; and 2,4,6-trinitrotoluene (TNT), a nitroarene. The first two are white powders, but they may be plasticized. TNT can range in appearance from a creamy white powder to a yellow solid. Because TNT is melt-castable, it is often the matrix for PETN or RDX, e.g. Pentalite or Comp B, respectively.

Figure 41:
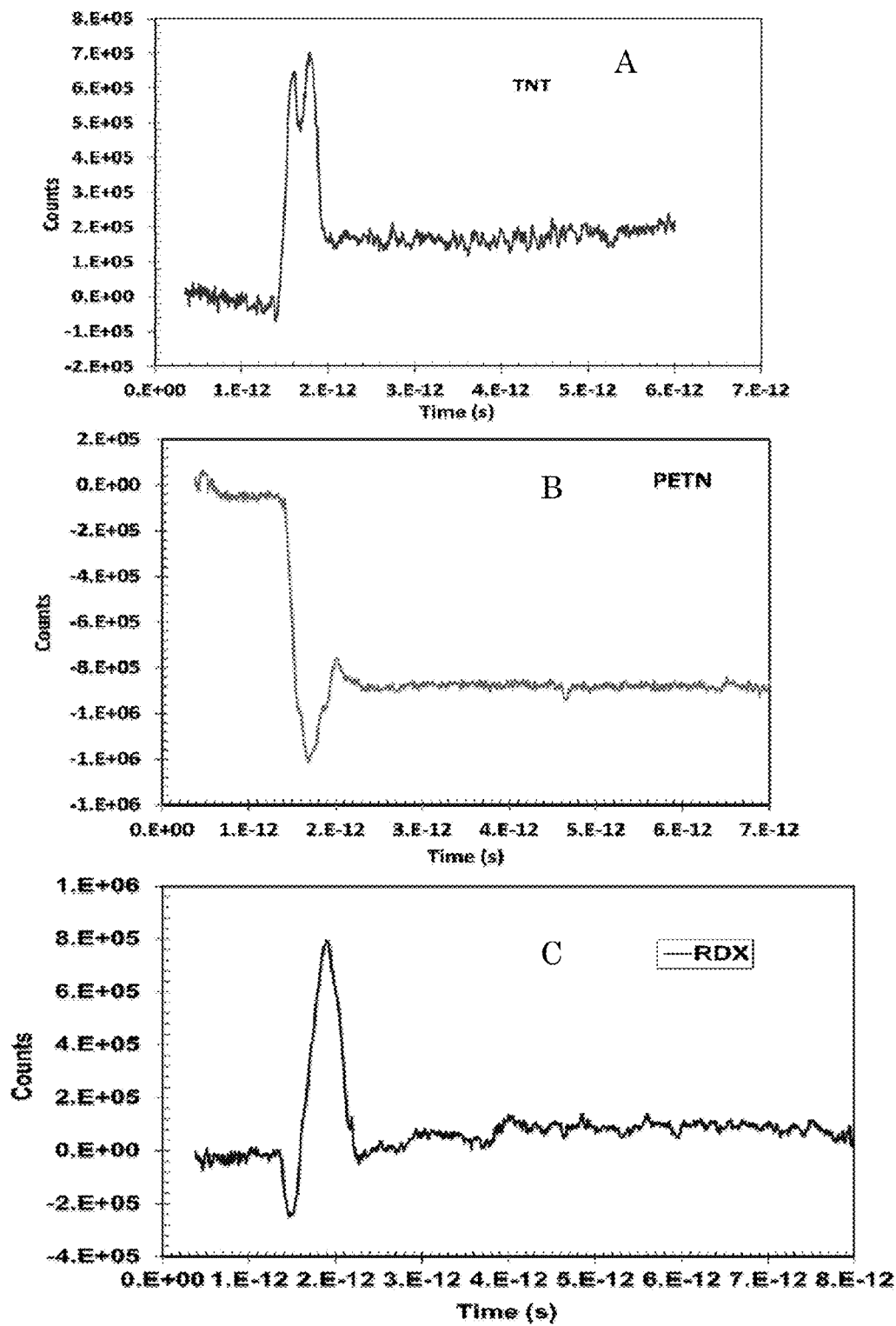
FIG. 41A-C show temporal signal (interferogram) of known explosive samples on glass slide.
Figure 42:
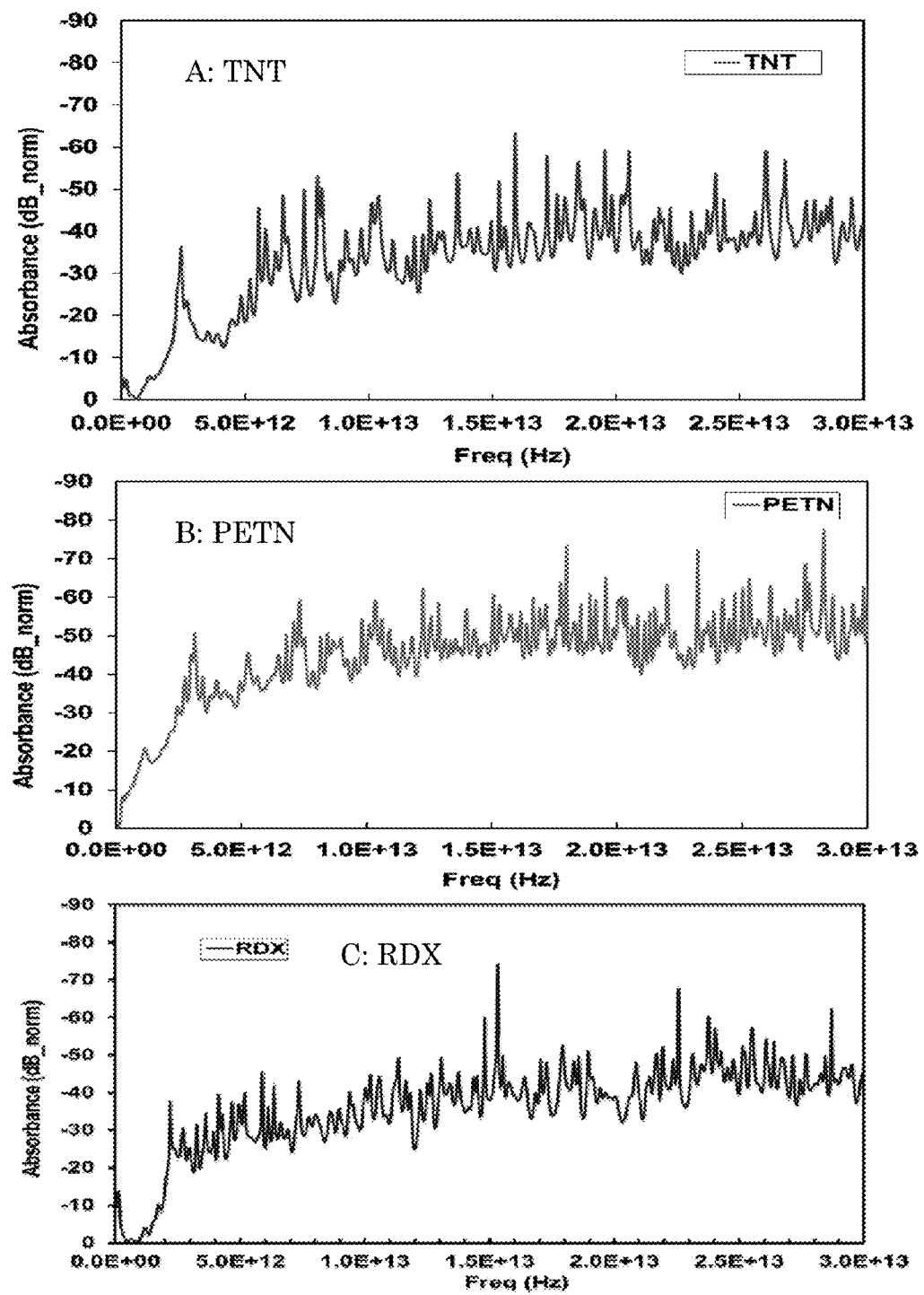
FIG. 42A-C show Fourier transform absorbance spectrum of the three explosives over 0.1 THz to 30 THz: A: TNT, B: PETN, and C: RDX.

TNT, PETN and RDX samples were prepared as 1 mg/mL solution in methanol. An aliquot (30 µL) of each solution was dispensed on a glass slide that was dried at ~45° C. for 10 minutes. Each glass slide with resulting spot was mounted on a XYZ-stage and placed in the beam path of a terahertz spectrometer (TeraSpectra, Applied Research and Photonics) such that the beam is vertical to the sample plane. Respective temporal signals were acquired in transmission mode. FIGS. 41A-C show the temporal signals (interferogram) of all three samples. As can be seen, each temporal signal is distinctively different in both magnitude and shape, thus exhibiting unique features for identifying the compound. FIGS. 42A-C show the Fourier transform absorbance spectra of the respective samples over a range of ~0.1 THz to 30 THz. Here also the spectra exhibit distinct features for each compound. Within each spectrum there exist distinct absorption peaks that can be used to identify the species.

Since terahertz radiation is sensitive to the vibrational states of the entire molecule (as opposed to a bond vibration or its rotation), the absorbance peaks in FIGS. 42A-C correspond to the vibrational states of the molecules of the present investigation. However, further investigation is necessary to establish a relationship between the significant peaks with the molecular structure. Nevertheless, these initial spectra are promising and indicate the feasibility for further investigation within this region of rich spectral activities. For example, the observed trend in the RDX spectrum (FIG. 42C) matches with those reported within the first 4 THz.

Vibrational States of C60 and $H_2$@C60. The two molecules differ only by two Hydrogen atoms from one another and thus difficult to distinguish their spectral features using standard spectroscopy methods. Here, THz-TDS was used to determine the features in the respective spectra of the above two fullerenes.

Pure C60 and $H_2$@C60 was received in powder form and two solutions were prepared in 1,2-dicholorobenzene (solvent) via gravimetric method. C60: As received 5.09 mg C60 (solute) was added to 3.33863 g solvent, yielding a solution of 1.52458 mg/g. $H_2$@C60: As received 2 mg $H_2$@C60 (solute) was added to 1.30954 g solvent, producing a solution of 1.52725 mg/g. 30 µl of each solution (equivalent to ~45.818 µg solid) were dispensed on two glass slides and the resulting drops were allowed to dry on a hot plate at 45° C. for ~15 minutes. The slides were mounted on a XYZ stage one at a time and their spectra were acquired.

Figure 43:
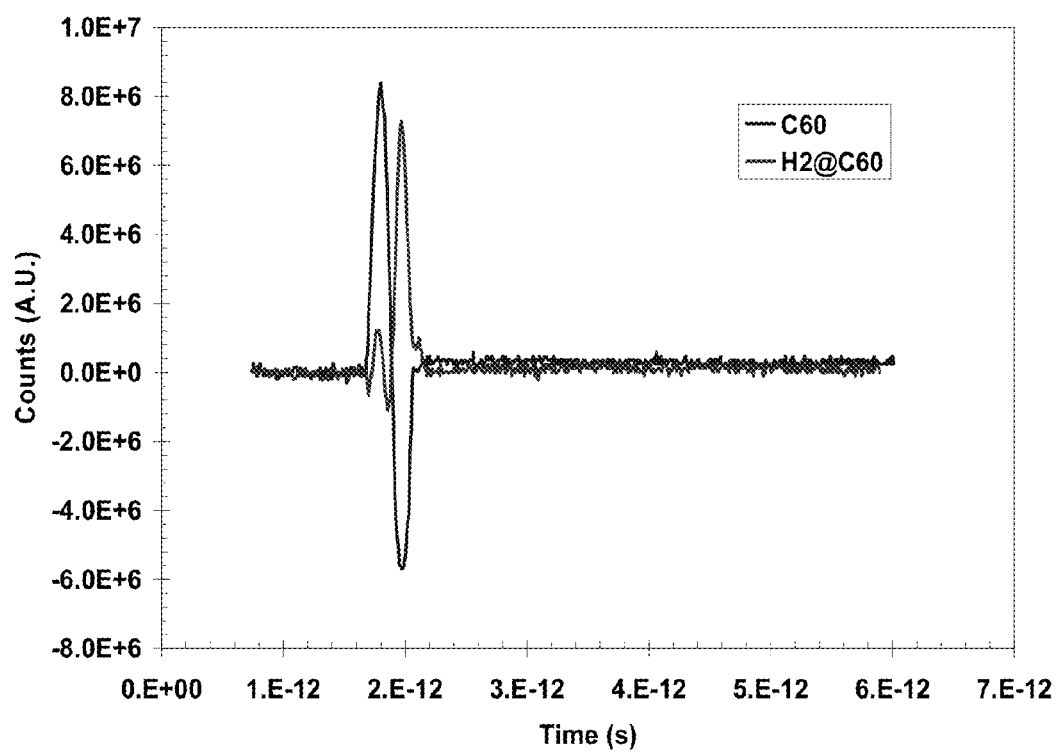
FIG. 43 shows time domain signal of C60 and $H_2$@C60.
Figure 44:
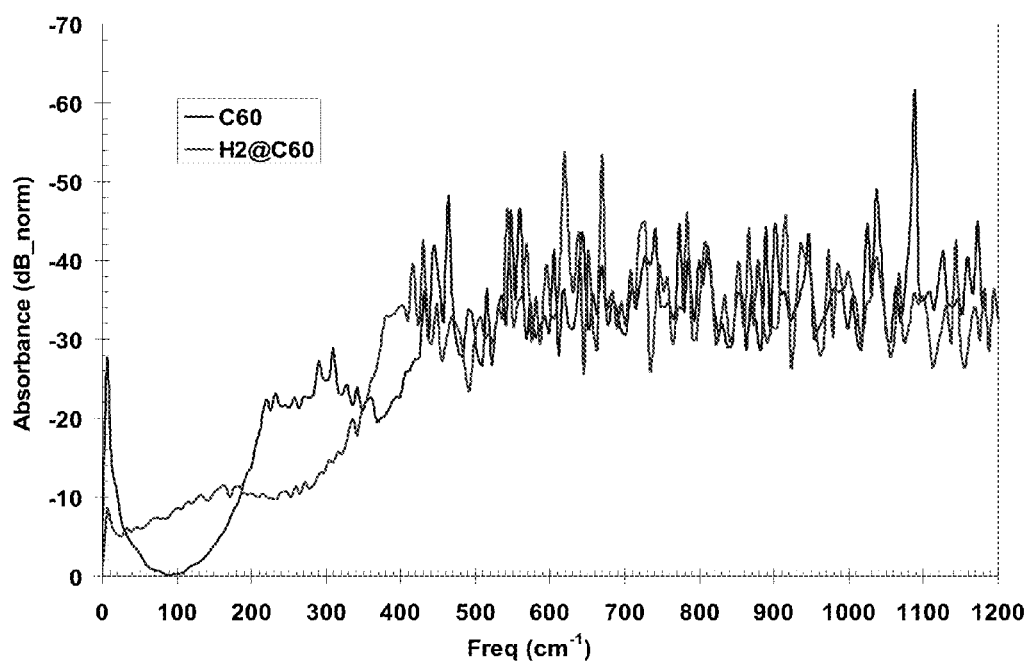
FIG. 44 Fourier transform frequency spectra of C60 and $H_2$@C60 show distinct absorbance characteristics.

FIG. 43 shows the time domain temporal signal of both samples. The $H_2$@C60 pulse shows lower peak height compared to pure C60 as well as different peak positions. FIG. 44 exhibits the Fourier transform absorbance spectra of the two Fullerenes obtained from their respective pulses that show distinctively different peaks compared to each other. Table 1 summarizes the absorbance peaks for both C60 and $H_2$@C60 extracted from their spectra and also those obtained from IR spectra.

TABLE 1

Table 1. Comparison of IR and THz spectra of $C_{60}$ and $H_2$@$C_{60}$. All units are in $cm^{-1}$.

| $C_{60}$: THz [present study] | $C_{60}$: Ref. [23] | $H_2$@$C_{60}$: THz [present study] | $H_2$@$C_{60}$: Ref. [23] |
|---|---|---|---|
| 6.44, 219, 232, 258, 271, 290 | — | 6.32, 164, 183 | — |
| 309, 328, 341, 361, 393 | — | 335, 379 | — |
| 406, 432, 444, 464, 490 | — | 404, 417, 430, 449, 468 | — |
| 515, 535, 543, 560, 593 | 526.6, 576.7 | 506, 543, 569, 581, 594 | 526.5, 576.7 |

TABLE 1-continued

Table 1. Comparison of IR and THz spectra of $C_{60}$ and $H_2@C_{60}$. All units are in $cm^{-1}$.

| $C_{60}$: THz [present study] | $C_{60}$: Ref. [23] | $H_2@C_{60}$: THz [present study] | $H_2@C_{60}$: Ref. [23] |
|---|---|---|---|
| 605, 618, 644, 670 | — | 619, 638, 651, 670 | — |
| 740, 772 | — | 708, 727, 746, 784 | — |
| 857, 889 | — | 809, 834, 853, 866, 878 | — |
| 902, 947, 992 | — | 916, 935, 973, 986, 998 | — |
| 1024, 1037, 1088 | — | 1036, 1068, 1087 | — |
| 1127, 1159, 1172 | 1182.3, 1429.2 | 1131, 1144, 1169, 1182, 1194 | 1182.3, 1429.2 |
| Total: 38 | 4 | 41 | 4 |

As seen from Table 1, there is a number of absorbance peaks present in the THz spectra that were not detected by the IR spectra. This is indicative of the sensitivity obtainable from THz interaction with the entire molecule. That is as the molecular conformation change as a function of time-dependent stimulus on the femto- to pico-second scale (or, equivalently, the frequency of the stimulus on the THz scale), the absorbance is directly probed and recorded by the detection system. While some far lying states (e.g., 4250 cm-1) were observed by low-temperature (6K) IR spectroscopy and explained by translational and rotational motions of $H_2$ inside C60 cage, those studies were also limited to the detection of only a few number of states. The observation of multiple states in the low frequency region indicates that the vibrational states of these molecules can be effectively probed by THz.

An important ability of the Fullerene research is the possibility of controlling the spin selectivity of the catalyzed conversion of the para species, $pH2@C60$, into the ortho species, $oH_2@C60$, so that a strong nuclear spin polarization may be produced. However, if spin selective $H_2@C60$ is produced, it seems to be difficult for standard IR spectroscopy to easily distinguish and identify the ortho and para states. The presence of distinguishable absorbance peaks identified by THz spectra suggests that this tool has the required sensitivity for detecting the spin isomers of $H_2$ inside C60. Additionally, the presence of additional peaks indicates that this method can detect modes not visible in standard IR, yielding unique insight into uncharacterized host/guest interactions.

Table 2 summarizes the predicted states of C60 (col. 2) and also the measured states of the present study (col. 1).

TABLE 2

Table 2. Comparison of IR and THz spectra of $C_{60}$ and $H_2@C_{60}$. All units are in $cm^{-1}$.

| $C_{60}$: THz [present study] | $C_{60}$: Ref. [23] |
|---|---|
| 6.44, 219, 232, 258, 271, 290 | 272 |
| 309, 328, 341, 361, 393 | 343, 353 |
| 406, 432, 444, 464, 490 | 403, 433, 485, 496 |
| 515, 535, 543, 560, 593 | 526, 534, 553, 567, 568, 575 |
| 605, 618, 644, 670 | 668 |
| 740, 772 | 709, 736, 743, 753, 756, 764, 772, 776, 796 |
| 857, 889 | 831 |
| 902, 947, 992 | 961, 973, 984 |
| 1024, 1037, 1088 | 1079, 1099 |
| 1127, 1159, 1172 | 1182 |
| Total: 38 | 30 |

Modes whose frequencies appear in bold type (Table 2, col. 2) have been unequivocally identified from Raman, IR, neutron, or fluorescence experiments. Moreover, each of the states enumerated in col. 2 have associated degeneracies; e.g., the state at 272 cm-1 has a degeneracy of 5 and so on. The main inference is that the terahertz spectra clearly shows difference between C60 and $H_2@C60$.

For all the molecular systems studied, no two molecule exhibit exactly identical absorbance peaks. This is primarily due to two prominent features of the underlying technology: (1) very high sensitivity available from the TeraSpectra down to parts per trillion[8] and (2) a wide window over 0.1 THz to ~35 THz. There are many molecular systems, especially the ones having close molecular weight, may exhibit similar trend within a narrower window of observation (e.g., 0-3 THz), but over a broadband window of observation of the present study, the difference between two molecules even of very close molecular weight become clear.

Thus, it is evident that the THz-TDS provides a suitable tool to continue both theoretical and experimental work with the vibrational states of the Fullerenes and other molecular system.

Broadband terahertz radiation has been generated from electro-optic Dendrimer via difference frequency method (two-photon excitation). A sharp time-domain pulse is obtained by standard electro-optic sampling method of detection. The Fourier spectrum obtained from the time-domain pulse spans up to ~35 THz. This wider THz range is expected to aid in high sensitivity characterization of molecular interactions because terahertz radiation is sensitive to the vibrational states of an entire molecule (as opposed to bond or torsional vibrations, or charge state that are usually probed by other methods). Two examples of application have been outlined. It has been shown that common explosive traces can be uniquely identified by their THz spectra. It is also shown that the vibrational states of two Fullerenes having very close molecular weights can also be uniquely probed for their vibrational states.

It is to be understood that the figures and descriptions of embodiments of the system have been simplified to illustrate elements that are relevant for a clear understanding, while eliminating, for the purpose of clarity, many other elements found in typical systems. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

Other embodiments of the invention will be apparent to those skilled in the art from a consideration of this specification or practice of the invention disclosed herein; the scope and spirit of the invention being indicated by the following claims.

What is claimed is:

1. A terahertz scanning reflectometer for layer thickness determination, comprising:

a continuous wave terahertz source configured to generate terahertz radiation toward a reference layer and a target layer, wherein the reference layer and the target layer have a related base structure;

a first detector configured to detect a reference layer reflected beam from the reference layer responsive to the terahertz radiation;

a second detector configured to detect a target layer reflected beam from the target layer responsive to the terahertz radiation; and a processor configured to determine a difference between the reference layer reflected beam and target layer reflected beam, wherein the continuous wave terahertz source includes a pump laser in line with a neutral density filter, a mirror, an emitter and aperture and an IR filter, the continuous wave terahertz source feeds parabolic mirrors and beamsplitters to forward the terahertz radiation which includes a terahertz beam directed to the reference layer and another terahertz beam directed to the target layer.

2. The terahertz scanning reflectometer of claim 1, wherein multiple detectors are deployed for faster scanning of semiconductor wafers.

3. The terahertz scanning reflectometer of claim 1, wherein scanning resolution for a surface layer is at a resolution of 23.84 nanometer or lower.

4. The terahertz scanning reflectometer of claim 1, wherein sub-surface layers of a multi-layer substrate are scanned on a layer-by-layer basis.

5. The terahertz scanning reflectometer of claim 1, wherein a layer structure of a multi-layer substrate is detected and identified.

6. The terahertz scanning reflectometer of claim 1, wherein defects are detected on a surface and in a sub-surface layer of a multi-layered substrate.

7. The terahertz scanning reflectometer of claim 6, wherein the defects are inclusion, crack, non-uniformity, dislocation, phase change, and new phase formation.

8. The terahertz scanning reflectometer of claim 1, wherein the difference is based on measuring material properties including effective density, effective dielectric constant, and effective refractive index.

* * * * *